US011000710B2

(12) United States Patent
Grootveld et al.

(10) Patent No.: US 11,000,710 B2
(45) Date of Patent: May 11, 2021

(54) COMPOSITION AND METHOD FOR THE GENERATION OF CHLORINE DIOXIDE FROM THE OXIDATIVE CONSUMPTION OF BIOMOLECULES

(71) Applicant: Micropure, Inc., Scottsdale, AZ (US)

(72) Inventors: Martin C. Grootveld, Greater Manchester (GB); Christopher J. L. Silwood, Middlesex (GB); James L. Ratcliff, Pueblo West, CO (US)

(73) Assignee: Micropure, Inc., Scottsdale, AZ (US)

(*) Notice: Subject to any disclaimer, the term of this patent is extended or adjusted under 35 U.S.C. 154(b) by 0 days.

(21) Appl. No.: 15/605,506

(22) Filed: May 25, 2017

(65) Prior Publication Data

US 2017/0319877 A1 Nov. 9, 2017

Related U.S. Application Data

(63) Continuation of application No. 12/704,360, filed on Feb. 11, 2010, now abandoned.

(60) Provisional application No. 61/152,336, filed on Feb. 13, 2009.

(51) Int. Cl.
*A61Q 11/00* (2006.01)
*A61K 8/20* (2006.01)
*A61K 33/20* (2006.01)

(52) U.S. Cl.
CPC ............. *A61Q 11/00* (2013.01); *A61K 8/20* (2013.01); *A61K 33/20* (2013.01)

(58) Field of Classification Search
CPC ....................................................... A61K 7/20
USPC ........................................................ 424/53
See application file for complete search history.

(56) References Cited

U.S. PATENT DOCUMENTS

| | | | |
|---|---|---|---|
| 2,451,897 A | 10/1948 | Woodward | |
| 2,482,891 A | 9/1949 | Mathieson | |
| 3,271,242 A | 9/1966 | McNicholas et al. | |
| 4,084,747 A | 4/1978 | Alliger | |
| 4,330,531 A | 5/1982 | Alliger | |
| 4,420,471 A | 12/1983 | Elton | |
| 4,499,077 A | 2/1985 | Stockel et al. | |
| 4,552,679 A | 11/1985 | Schobel et al. | |
| 4,689,215 A | 8/1987 | Ratcliff | |
| 4,696,811 A | 9/1987 | Ratcliff | |
| 4,786,492 A | 11/1988 | Ratcliff | |
| 4,788,053 A | 11/1988 | Ratcliff | |
| 4,792,442 A | 12/1988 | Ratcliff | |
| 4,793,989 A | 12/1988 | Ratcliff | |
| 4,808,389 A | 2/1989 | Ratcliff | |
| 4,818,519 A | 4/1989 | Ratcliff | |
| 4,837,009 A | 6/1989 | Ratcliff | |
| 4,851,213 A | 7/1989 | Ratcliff | |
| 4,855,135 A | 8/1989 | Ratcliff | |
| 4,861,514 A | 8/1989 | Hutchings | |
| 4,886,657 A | 12/1989 | Ratcliff | |
| 4,889,714 A | 12/1989 | Ratcliff | |
| 4,891,216 A | 1/1990 | Kross et al. | |
| 4,902,498 A | 2/1990 | Agricola et al. | |
| 4,925,656 A | 5/1990 | Ratcliff | |
| 4,963,346 A | 10/1990 | Amer | |
| 4,975,285 A | 12/1990 | Ratcliff | |
| 5,192,691 A | 3/1993 | Quinn et al. | |
| 5,200,171 A | 4/1993 | Ratcliff | |
| 5,281,412 A | 1/1994 | Lukacovic et al. | |
| 5,284,648 A | 2/1994 | White et al. | |
| 5,348,734 A | 9/1994 | Ratcliff | |
| 5,364,462 A | 11/1994 | Crystal et al. | |
| 5,389,384 A | 2/1995 | Jooste | |
| 5,489,435 A | 2/1996 | Ratcliff | |
| 5,616,347 A | 4/1997 | Alliger et al. | |
| 5,618,550 A | 4/1997 | Ratcliff | |
| 5,667,817 A | 9/1997 | Kross | |
| 5,707,975 A | 1/1998 | Francois et al. | |
| 5,738,840 A | 4/1998 | Richter | |
| 5,772,986 A | 6/1998 | Kross | |
| 5,811,115 A | 9/1998 | Ratcliff | |
| 5,834,003 A | 11/1998 | Ratcliff | |
| 5,902,575 A | 5/1999 | Ratcliff | |
| 5,935,592 A | 8/1999 | Ratcliff | |
| 6,017,554 A | 1/2000 | Ratcliff | |
| 6,039,934 A | 3/2000 | Alliger | |
| 6,077,502 A | 6/2000 | Witt et al. | |
| 6,106,293 A | 8/2000 | Wiesel et al. | |
| 6,132,702 A | 10/2000 | Witt et al. | |
| 6,136,348 A | 10/2000 | Ratcliff et al. | |

(Continued)

FOREIGN PATENT DOCUMENTS

| | | |
|---|---|---|
| JP | 6054311 | 3/1985 |
| WO | 0613678 | 9/1994 |
| WO | 2003022256 | 3/2003 |
| WO | 2009009162 | 1/2009 |
| WO | 2009009163 | 1/2009 |
| WO | 2011119177 | 9/2011 |
| WO | 2012051727 | 4/2012 |
| WO | 2019046841 | 3/2019 |

OTHER PUBLICATIONS

USPTO; Final Office Action dated Jun. 6, 2018 in U.S. Appl. No. 11/774,730.

(Continued)

*Primary Examiner* — Walter E Webb
(74) *Attorney, Agent, or Firm* — Snell & Wilmer LLP

(57) ABSTRACT

The composition and method for the use of stabilized chlorine dioxide as an antimicrobial agent against oral microorganisms for the treatment and prevention of halitosis and prevention of oral diseases, wherein the activation and release of chlorine dioxide from the composition a) occurs rapidly and without a period of induction, b) results from the oxidative reduction and consumption of amino acids and volatile sulfur compound precursors, and c) generates twice the available chlorine dioxide gas as that generated from simply lowering the pH of the composition. The preferred concentrations of stabilized chlorine dioxide in this invention are in the range of 0.005% to 2.0% (w/v) wherein the pH of the composition is initially lowered by a citrate and then stabilized by a peroxy compound.

10 Claims, 6 Drawing Sheets

(56) References Cited

U.S. PATENT DOCUMENTS

| | | | |
|---|---|---|---|
| 6,231,830 B1 | 5/2001 | Madray | |
| 6,235,269 B1 | 5/2001 | Witt et al. | |
| 6,251,372 B1 | 6/2001 | Witt et al. | |
| 6,264,924 B1 | 7/2001 | Witt et al. | |
| 6,280,716 B1 | 8/2001 | Ratcliff | |
| 6,280,775 B1 | 8/2001 | Sasson et al. | |
| 6,291,166 B1 | 9/2001 | Gerdes et al. | |
| 6,325,997 B1 | 12/2001 | Christopfel | |
| 6,350,438 B1 | 2/2002 | Witt et al. | |
| 6,375,933 B1 | 4/2002 | Subramanyam | |
| 6,391,577 B1 | 5/2002 | Mikkelsen et al. | |
| 6,582,682 B2 | 6/2003 | Stier | |
| 6,696,047 B2 | 2/2004 | Scott et al. | |
| 6,780,838 B2 | 8/2004 | Lipton et al. | |
| 6,846,478 B1 | 1/2005 | Doyle et al. | |
| 6,929,790 B2 * | 8/2005 | Kleinberg | A61K 8/27 424/49 |
| 7,087,228 B2 | 8/2006 | Goodman | |
| 7,387,774 B2 | 6/2008 | Faller et al. | |
| 7,737,166 B2 | 6/2010 | Kawakami et al. | |
| 8,252,771 B2 | 8/2012 | Uecht et al. | |
| 8,697,141 B2 | 4/2014 | Ratcliff | |
| 8,906,348 B2 | 12/2014 | Narasimhan et al. | |
| 8,926,951 B2 | 1/2015 | Ratcliff | |
| 9,682,023 B2 | 6/2017 | Ratcliff | |
| 9,937,204 B2 | 4/2018 | Young et al. | |
| 2002/0028324 A1 | 3/2002 | Koichi et al. | |
| 2002/0197215 A1 | 12/2002 | Stier | |
| 2003/0066336 A1 | 4/2003 | Kotsuka et al. | |
| 2003/0129144 A1 | 7/2003 | Scott | |
| 2005/0084551 A1 | 4/2005 | Jensen et al. | |
| 2005/0196370 A1 | 9/2005 | Yu et al. | |
| 2005/0234545 A1 | 10/2005 | Su et al. | |
| 2007/0190176 A1 | 8/2007 | Percival et al. | |
| 2008/0055154 A1 | 3/2008 | Martucci et al. | |
| 2008/0247973 A1 | 10/2008 | Baig et al. | |
| 2008/0269353 A1 | 10/2008 | Takada et al. | |
| 2009/0016973 A1 | 1/2009 | Ratcliff | |
| 2010/0009009 A1 | 1/2010 | Young et al. | |
| 2010/0015207 A1 | 1/2010 | Speronello et al. | |
| 2010/0221198 A1 | 9/2010 | Ratcliff | |
| 2010/0233101 A1 | 9/2010 | Grootveld et al. | |
| 2011/0318282 A1 | 12/2011 | Ratcliff et al. | |
| 2012/0034280 A1 | 2/2012 | Cohen et al. | |
| 2012/0164084 A1 | 6/2012 | Ratcliff et al. | |
| 2012/0201899 A1 | 8/2012 | McWhorter et al. | |
| 2015/0017107 A1 | 1/2015 | Hill | |
| 2015/0297478 A1 | 10/2015 | Ratcliff | |
| 2017/0216351 A1 | 8/2017 | Young et al. | |
| 2019/0070085 A1 | 3/2019 | Shewale et al. | |

OTHER PUBLICATIONS

USPTO; Office Action dated Aug. 20, 2008 in U.S. Appl. No. 11/774,730.
USPTO; Final Office Action dated Mar. 3, 2009 in U.S. Appl. No. 11/774,730.
USPTO; Advisory Action dated Jul. 10, 2009 in U.S. Appl. No. 11/774,730.
USPTO; Office Action dated Nov. 9, 2009 in U.S. Appl. No. 11/774,730.
USPTO; Office Action dated Feb. 22, 2010 in U.S. Appl. No. 11/774,789.
USPTO; Final Office Action dated Jun. 29, 2010 in U.S. Appl. No. 11/774,730.
USPTO; Notice of Allowance dated Sep. 29, 2010 in U.S. Appl. No. 11/774,789.
USPTO; Advisory Action dated Dec. 17, 2010 in U.S. Appl. No. 11/774,730.
USPTO; Restriction Requirement dated Apr. 29, 2011 in U.S. Appl. No. 12/547,420.
USPTO; Office Action dated May 31, 2011 in U.S. Appl. No. 12/547,420.
USPTO; Office Action dated Jul. 19, 2011 in U.S. Appl. No. 11/774,730.
USPTO; Final Office Action dated Feb. 13, 2012 in U.S. Appl. No. 12/547,420.
USPTO; Final Office Action dated Mar. 23, 2012 in U.S. Appl. No. 11/774,730.
USPTO; Advisory Action dated Jul. 19, 2012 in U.S. Appl. No. 12/547,420.
USPTO; Advisory Action dated Oct. 17, 2012 in U.S. Appl. No. 11/774,730.
USPTO; Office Action dated Jun. 20, 2013 in U.S. Appl. No. 11/774,730.
USPTO; Final Office Action dated Nov. 27, 2013 in U.S. Appl. No. 11/774,730.
USPTO; Notice of Allowance dated Dec. 2, 2013 in U.S. Appl. No. 12/547,420.
USPTO; Advisory Action dated Apr. 1, 2014 in U.S. Appl. No. 11/774,730.
USPTO; Advisory Action dated Jun. 3, 2014 in U.S. Appl. No. 11/774,730.
USPTO; Office Action dated Nov. 28, 2014 in U.S. Appl. No. 11/774,730.
USPTO; Final Office Action dated May 4, 2015 in U.S. Appl. No. 11/774,730.
USPTO; Advisory Action dated Aug. 24, 2015 in U.S. Appl. No. 11/774,730.
USPTO; Office Action dated Oct. 7, 2015 in U.S. Appl. No. 11/774,730.
USPTO; Restriction Requirement dated Sep. 14, 2011 in U.S. Appl. No. 12/731,271.
USPTO; Office Action dated Oct. 19, 2011 in U.S. Appl. No. 12/731,271.
USPTO; Final Office Action dated Jan. 9, 2014 in U.S. Appl. No. 12/731,271.
USPTO; Advisory Action dated Apr. 1, 2014 in U.S. Appl. No. 12/731,271.
USPTO; Notice of Allowance dated Nov. 3, 2014 in U.S. Appl. No. 12/731,271.
USPTO; Restriction Requirement dated Feb. 28, 2013 in U.S. Appl. No. 13/115,815.
USPTO; Office Action dated Jun. 4, 2013 in U.S. Appl. No. 13/115,815.
USPTO; Final Office Action dated Mar. 13, 2014 in U.S. Appl. No. 13/115,815.
USPTO; Advisory Action dated Jul. 24, 2014 in U.S. Appl. No. 13/115,815.
USPTO; Office Action dated Apr. 24, 2015 in U.S. Appl. No. 13/115,815.
USPTO; Final Office Action dated Nov. 20, 2015 in U.S. Appl. No. 13/115,815.
USPTO; Office Action dated Jul. 26, 2016 in U.S. Appl. No. 14/589,260.
USPTO; Office Action dated Aug. 11, 2015 in U.S. Appl. No. 14/192,195.
USPTO; Final Office Action dated Jan. 7, 2016 in U.S. Appl. No. 14/192,195.
USPTO; Advisory Action dated Apr. 20, 2016 in U.S. Appl. No. 14/192,195.
USPTO; Office Action dated Jun. 16, 2016 in U.S. Appl. No. 14/192,195.
USPTO; Notice of Allowance dated Feb. 16, 2017 in U.S. Appl. No. 14/589,260.
USPTO; Final Office Action dated Nov. 1, 2017 in U.S. Appl. No. 13/131,506.
USPTO; Office Action dated Jan. 22, 2018 in U.S. Appl. No. 11/774,730.
PCT; International Search Report dated Feb. 27, 2008 in Application No. PCT/US2008/55154.
PCT; Written Opinion dated Jun. 26, 2008 in Application No. PCT/US2008/55154.
PCT; International Preliminary Report on Patentability dated Aug. 25, 2009 in International Application No. PCT/US2008/55154.

(56) References Cited

OTHER PUBLICATIONS

PCT; Written Opinion dated Jul. 30, 2010 in International Application PCT/US2010/037768.
PCT; International Search Report dated Jul. 30, 2010 in International Application No. PCT/US2010/037768.
USPTO; Notice of Allowance dated Nov. 27, 2017 in U.S. Appl. No. 15/475,006.
JPO; Office Action dated Dec. 21, 2012 in Japanese Application No. 2010-516078.
JPO; Office Action dated Jun. 19, 2013 in Japanese Application No. 2010-516078.
JPO; Report of Pretrial Reconsideration dated Dec. 12, 2013 in Japanese Application No. 2010-516078.
JPO; Office Action dated Nov. 11, 2014 in Japanese Application No. 2013-217385.
JPO; Office Action dated Aug. 17, 2015 in Japanese Application No. 2013-217385.
JPO; Office Action dated Apr. 4, 2016 in Japanese Application No. 2013-217385.
3M Peridex CHG 0.12% Oral Rinse; MSDS No. 25/8627-9 [Online]; 3M: St Paul, MN, http://library.queensu.ca/research/guide/how-cite-chemical-literature/material-safety-data-sheets (2011). (Applicant makes no representation regarding the content of the information on the website, nor does Applicant make any representation as to the date any of the content that may be on the website was made publicly available.).
Aas, JA. et al., "Defining the normal bacterial flora of the oral cavity," J Clinical Microbial, 43(11), pp. 5721-5732, (2005).
Armitage GC, "Clinical evaluation of periodontal disease." Periodontal 2000, vol. 7, pp. 39-53, (1995).
Baehni PC, et al., "Anti-plaque agents in the prevention of biofilm-associated oral diseases," Oral Diseases, 9, pp. 23-29, (2003).
Barnhart, et al., "Dentifrice usage and ingestion among four age groups," J. Dent Res, 53, pp. 1317-1322, (1976).
Bassani DG, Olinto MTA, Krieger N. "Periodontal disease and perinatal outcomes: a case control study," J Clinical Periodontal, vol. 34, pp. 31-39, (2007).
Beck J, Garcia R, Heiss G, "Vokonas PS, Offenbacher S., Periodontal disease and cardiovascular disease," J Periodontal, vol. 67, pp. 1123-1137, (1996).
Boggess et al., "Fetal immune response to oral pathogens and risk of preterm birth," American Journal of Obstetrics and Gynecology, vol. 193, pp. 1121-1126, (2005).
Bolstad Al. et al., "Taxonomy, Biology, and Periodontal Aspects of Fusobacterium Nucleatum," Clinical Microbiology Reviews, vol. 9(1), pp. 55-71, (1996).
Botha SJ. Etal., "Effective Inhibition of Oral Organisms by Chlorine Dioxide ($ClO_2$)," The Preliminary Program for Scientific Meeting of the South African Division of IADR, (Sep. 2006).
Briggs et al., "Angiographically Confirmed Coronary Heart Disease and Periodontal Disease in Middle-Aged Males," J. Periodontal, vol. 77(1), pp. 95-102, (2006).
Buduneli et al., "Periodontal Infections and Pre-Term Birth Weight: a case control study," J. Clinical Periodontal, vol. 32, pp. 174-181, (2005).
Corbin, et al., "Antimicrobial penetration and efficacy in an In Vitro oral biofilm model," Anti-microbiology Agents Chemo Therapy, vol. 55(7), pp. 3338-3344, (2011).
Daily Med: "Current Medication Information. Chlorhexidine Gluconate Rinse [Xttrium Laboratories, Inc.]," Available at: http://dailymed.nlm.nih.gov/dailymed/lookup.cfm?setid=34d15e72-8770-49dc-a514-d44ae4468ale, (2010). (Applicant makes no representation regarding the content of the information on the website, nor does Applicant make any representation as to the date any of the content that may be on the website was made publicly available.).
Daily Med: "Current Medication Information. Periogard (chlorhexidine gluconate) liquid [Colgate-Palmolive Company]," Available at: http://dailymed.nlm.nih.gov/dailymed/lookup.cfm?setid=6e537d5f-bce1-41ce-9984-9b3c2861b7c9, (2010). (Applicant makes no representation regarding the content of the information on the website, nor does Applicant make any representation as to the date any of the content that may be on the website was made publicly available.).
Daniel FB, et al., "Comparative Sub chronic Toxicity Studies of Three Disinfectants," J Am Water Works Ass, 10, pp. 61-69, (1990).

Drake, "Final Report: Phase III Biofilm Studies," Rowpar Pharmaceuticals, Inc., (2008).
Ford et al., "Cross-Reactivity of GroEL Antibodies with Human Heat Shock Protein 60 and Quantification of Pathogens in Atherosclerosis," Oral Microbiology Immunology, vol. 20, pp. 296-302, (2005).
Ford et al., "Anti-P Gingivalis Response Correlates with Atherosclerosis," Journal of Dental Research, vol. 86(1), pp. 35-40, (2007).
Frascella et al., "Odor Reduction Potential of a Chlorine Dioxide Mouth rinse," Journal of Clinical Dentistry, vol. 9, pp. 39-42, (1998).
Frontier Pharmaceutical Inc., "The DioxiCare System," http://www.frontierpharm.com/dioxicare-system.php. (Last visited Aug. 5, 2008). (Applicant makes no representation regarding the content of the information on the website, nor does Applicant make any representation as to the date any of the content that may be on the website was made publicly available.).
Garcia et al., "Relationship Between Periodontal Disease and Systemic Health," Periodontology 2000, vol. 25, pp. 21-36, (2001).
Grau et al., "Periodontal Disease as a Risk Factor for Ischemic Stroke," Stroke, vol. 35(2), pp. 496-501, (2004).
Grootveld, et al., "H NMR-Linked Chemo metric Analysis of Control and Dentifrice-Treated Human Saliva," IADR/AADR/CADR 87th General Session and Exhibition, (2009).
Han et al., "Fusobacterium Nucleatum Induces Premature and Term Still Births in Pregnant Mice: Implication of Oral Bacterial in Preterm Birth," Infection and Immunity, vol. 72(4), pp. 2272-2279, (2004).
Herzbert et al., "Dental Plaque, Platelets, and Cardiovascular Diseases," Ann Periodontal, vol. 3, pp. 151-160, (1998).
Hojo et al., "Bacterial interaction in dental biofilm development," Journal of Dental Research, vol. 88, pp. 982-990, (2009).
Holt et al., "Porphyromonas Gingivalis, Treponema Denticola, and Tannerella Forsythias: the Red Complex, a Prototype Polybacterial Pathogenic Consortium in Periodontitis," Periodontology 2000, vol. 38, pp. 72-122, (2005).
"Ingredients: Tetra sodium Pyrophosphate," http://sci-toys.com/ingredients/tetrasodium_pyrophosphate.html., (2011). (Applicant makes no representation regarding the content of the information on the website, nor does Applicant make any representation as to the date any of the content that may be on the website was made publicly available.).
Jess et al., Spratt "Dental Plaque and Bacterial Colonization," Medical Biofilms, Chapter 4.1, pp. 173-198, (2003).
Kazor et al., "Diversity of bacterial Populations on the Tongue Dorsa of Patients with Halitosis and Healthy Patients," Journal of Clinical Microbiology, vol. 41(2), pp. 558-563, (2003).
Kim et al., "Periodontal Disease and Systemic Conditions: a Bi-Directional Relationship," Odontology, vol. 94, pp. 10-21, (2006).
Kubota et al., "Efficacy of Chlorine Dioxide: Gas against Porphyromonas gingivalis, Nihon Koku Implant Gakkai Shi," Japanese Society of Oral Implantology, vol. 18(2), pp. 222-228, (2005).
Lee et al., "Cytotoxicity of chlorhexidine on human osteoblastic cells is related to intracellular glutathione levels," Int. Endod. J., vol. 43(5), pp. 430-435, (2010).
Lessa et al., "Toxicity of chlorhexidine on odontoblast-like cells," J Application of Oral Science., vol. 18(1), pp. 50-58, (2010).
Levitt et al., "Antibiotics and Dental Biofilms, "The Journal of Professional Excellence, Dimensions of Dental Hygiene, vol. 10, pp. 56-59, (2012).
Lim et al., "Relationship Between Markers of Metabolic Control and Inflammation on Severity of Periodontal Disease in Patients with Diabetes Mellitus," Journal of Clinical Periodontal, vol. 34, pp. 118-123, (2007).
Loesche et al., "Microbiology and Treatment of Halitosis," Periodontology 2000, vol. 28, pp. 256-279, (2002).
Lubbers et al., "The effects of chronic administration of chlorine dioxide, chlorite and chlorate to normal healthy adult male volunteers," Journal of Environmental Pathology Toxicology Oncology., vol. 5(4-5), pp. 229-238, (1984).
Madianos et al., "Maternal Periodontitis and Prematurity, Part II: Maternal Infection and Fetal Exposure," Ann. Periodontal, vol. 6, pp. 175-182, (2001).

(56) References Cited

OTHER PUBLICATIONS

Marder et al., "Bisphosphonate-Associated Osteonecrosis: Experiences in a Private Practice," Dent Today, vol. 27(10), pp. 99-103, (2008).
Marsh, "Dental Plaque as a Microbial Biofilm," Caries Research, vol. 38, pp. 204-2011, (2004).
Marsh, "Dental Plaque: biological significance of a biofilm and community life-style," J Clinical Periodontal, vol. 32, pp. 7-15, (2005).
Masschelein W.J., "Chemical Oxidation: Technologies: Technologies for the Nineties," Lancaster Techonomic Publishing Company, vol. 1, pp. 170-192, (1992).
McBain AJ, et al., "Effects of a chlorhexidine Gluconate-Containing mouthwash on the vitality and antimicrobial susceptibility of in vitro oral bacterial ecosystems," Apl. Environment. Microbial, vol. 69(8), pp. 4770-4776, (2003).
Medical Subject Headings (MESH), http://www.ncbi.nlm.nih.gov/mesh._National_Library_ofMedicine, (2011). (Applicant makes no representation regarding the content of the information on the website, nor does Applicant make any representation as to the date any of the content that may be on the website was made publicly available.).
The Merck Index: An Encyclopedia of Chemicals, Drugs, and Biologicals, 12th Edition, Whitehouse Station, NJ; Merck & Co. Inc., (1996).
The Merck Index: An Encyclopedia of Chemicals, Drugs, and Biologicals, 14th Edition, Whitehouse Station, NJ; Merck & Co. Inc., (2006).
Michael GE, et al., "Chlorine dioxide water disinfection: A prospective epidemiology study," Arch Environ Health, vol. 36, pp. 20-27, (1981).
Michaud, "A Prospective Study of Periodontal Disease and Pancreatic Cancer in US Male Health Professionals," Journal of the National Cancer Institute, vol. 99(2), pp. 171-175, (2007).
Mullally BH et al., "Prevalence of Periodontal Pathogens in Localized and Generalized Forms of Early-Onset Periodontitis," Journal of Periodontal Research, vol. 35, pp. 232-241, (2000).
Nase et al., "Osteonecrosis of the jaw and oral bisphosphonate treatment," J Am Dent Association, vol. 137, pp. 1115-1119, (2006).
USP, "New or Revised Standards," http://www.usp.org/get-involved/partner/new-revised-standars, 2 Pgs., (Sep. 2017). (Applicant makes no representation regarding the content of the information on the website, nor does Applicant make any representation as to the date any of the content that may be on the website was made publicly available.).
Nishimura et al., "The Periodontal Host Response with Diabetes," Periodontology 2000, vol. 43, pp. 245-253, (2007).
Offenbacher et al., Maternal Periodontitis and Prematurity, Part I: Obstetric Outcome of Prematurity and Growth Restriction, Annual Periodontal, vol. 6, pp. 164-174, (2001).
Offenbacher et al., "Effects of Maternal Campylobacter Rectus Infection on Murine Placenta, Fetal and Neonatal Survival, and Brain Development," Journal of Periodontal, vol. 76, pp. 2133-2143, (2005).
Padilla et al., "Periodontal Pathogens in Atheromatous Plaques Isolated from Patients with Chronic Periodontitis," Journal of Periodontal Research, vol. 41, pp. 350-353, (2006).
Penn-Barwell JG et al., "Comparison of the antimicrobial effect of chlorhexidine and saline for irrigating a contaminated open fracture model," J Orthop. Trauma, (2012).
Rautemma et al., "Oral infections and systemic disease—an emerging problem in medicine," Clinical Microbial and Infect Diseases, vol. 13, pp. 1041-1047, (2007).
Ruggiero et al., "Osteonecrosis o the jaws and bisphosphonate therapy," J Dent Res., vol. 86, pp. 1013-1021, (2007).
Sedghizadeh et al., "Identification of microbial biofilms in osteonecrosis of the jaws secondary to bisphosphonate therapy," J Oral Maxillofacial Surg., vol. 66(4), pp. 767-775, (2008).
Sharon et al., "The effect of chlorhexidine mouth rinses on oral Candida in a group leukemic patients," Oral Surgery Oral Medicine Oral Pathology., vol. 44(2), pp. 201-205, (1977).
Shemesh et al., "The biocide chlorine dioxide stimulates biofilm formation in bacillus subtilis by Activation of the Histidine Kinase KinC," Journal of Bacteriology, vol. 192, pp. 6352-6356, (2010).
Shinada, et al., "Effects of a mouthwash with chlorine dioxide on oral malodor and salivary bacteria: a randomized placebo-controlled 7-day trial," Trials, vol. 11, (2010).
Socransky et al., "Microbial Complexes in Subgingival Plaque," Journal of Clinical Periodontal, vol. 25, pp. 134-144, (1998).
Soolari, et al., "Phosphate buffer-stabilized 0.1% chlorine dioxide containing mouth wash facilitted sequestration of Bisphosphonate Related Osteonecrosis of the jaw (BRONJ) lesion from a patient who presented with Osteonecrosis of the jaw and a history of intravenous bisphosphonate use: a case report," Translational Biomedicine, vol. 1, (2010).
Soolari, et al., "Closure of an open wound associated with bisphosphonate-related osteonecrosis of the jaw in a breast cancer patient," Open Dentistry Journal, vol. 5, pp. 1-5, (2011).
Speight, Lange's Handbook of Chemistry, 16th Edition, New York, McGraw-Hill, (2005).
US Code of Federal Regulations, Title 21: "Food and Drugs, Section 101.9 Nutrition Labeling of Food," (2011).
Villhauer A, et al., "Bactericidal Activity of Stabilized Chlorine Dioxide Rinse," American Association for Dental Research Meeting and Exhibition, (2008).
Werner et al., "Are alcohol containing mouthwashes safe?" Br Dent J., vol. 207(10), E19, pp. 488-489, (2009).
Wirthlin M.R. et al., "Effects of stabilized chlorine dioxide and chlorhexidine mouth rinses in vitro on cells involved in periodontal healing," J West Soc. Periodontal (Abstract only), vol. 54(3), pp. 67-71, (2006).
Yilmaz et al., "Intercellular Spreading of Porphyromonas Gingivalis Infection in Primary Gingival Epithelial Cells," Infection and Immunity, vol. 74(1), pp. 703-710, (2006).
Worthington H.V., et al,. Interventions for treating oral candidiasis for patients with cancer receiving treatment (Review), Cochrane Database of Systemic Reviews, Issue 2. Art. No. CD001972. DOI:10.1002/14651858. CD001972, pub3, 6 pgs, (2007).
Yu, D., et al., Caries Inhibition Efficacy of an Antiplaque/Antigingivitis Dentifrice; Am.Jour.Dent, 14, pp. 14C-17C (2000).
Zero, D.T., Dentifrices, Mouthwashes, and Remineralization/Caries Arrestment Strategies; BMC Oral Health, 6 (Suppl I):S9, 13 pgs (2006).
Office Action dated May 18, 2017 in U.S. Appl. No. 15/475,006.
Restriction Requirement dated Dec. 28, 2010 in U.S. Appl. No. 12/500,163.
Office Action dated Jan. 27, 2011 in U.S. Appl. No. 12/500,163.
Office Action dated May 26, 2011 in U.S. Appl. No. 12/704,360.
Final Office Action dated Oct. 19, 2011 in U.S. Appl. No. 12/500,163.
Final Office Action dated Dec. 2, 2011 in U.S. Appl. No. 12/704,360.
Advisory Action dated Mar. 5, 2012 in U.S. Appl. No. 12/500,163.
Office Action dated Dec. 19, 2012 in U.S. Appl. No. 12/704,360.
Restriction Requirement dated Mar. 28, 2013 in U.S. Appl. No. 13/131,506.
Restriction Requirement dated Apr. 22, 2013 in U.S. Appl. No. 13/131,506.
Final Office Action dated Aug. 26, 2013 in U.S. Appl. No. 12/704,360.
Office Action dated Jan. 24, 2014 in U.S. Appl. No. 12/500,163.
Advisory Action dated Feb. 12, 2014 in U.S. Appl. No. 12/704,360.
Office Action dated Apr. 10, 2014 in U.S. Appl. No. 12/704,360.
Office Action dated May 22, 2014 in U.S. Appl. No. 13/131,506.
Final Office Action dated Jul. 31, 2014 in U.S. Appl. No. 12/500,163.
Final Office Action dated Oct. 22, 2014 in U.S. Appl. No. 12/704,360.
Advisory Action dated Nov. 13, 2014 in U.S. Appl. No. 12/500,163.
Advisory Action dated Mar. 6, 2015 in U.S. Appl. No. 12/704,360.
Office Action dated Mar. 12, 2015 in U.S. Appl. No. 12/500,163.
Office Action dated Jun. 18, 2015 in U.S. Appl. No. 12/704,360.
Final Office Action dated Aug. 6, 2015 in U.S. Appl. No. 12/500,163.
Restriction Requirement dated Oct. 8, 2015 in U.S. Appl. No. 14/145,426.
Advisory Action dated Nov. 13, 2015 in U.S. Appl. No. 12/500,163.

(56) References Cited

OTHER PUBLICATIONS

Final Office Action dated Dec. 10, 2015 in U.S. Appl. No. 12/704,360.
Final Office Action dated Dec. 17, 2015 in U.S. Appl. No. 13/131,506.
Office Action dated Jan. 29, 2016 in U.S. Appl. No. 12/500,163.
Office Action dated Mar. 24, 2016 in U.S. Appl. No. 12/704,360.
Advisory Action dated Apr. 21, 2016 in U.S. Appl. No. 13/131,506.
Office Action dated May 20, 2016 in U.S. Appl. No. 14/145,426.
Final Office Action dated Sep. 30, 2016 in U.S. Appl. No. 12/500,163.
Final Office Action dated Nov. 25, 2016 in U.S. Appl. No. 12/704,360.
Office Action dated Dec. 23, 2016 in U.S. Appl. No. 13/131,506.
Abu-Elteen K.H., et al., , The prevalence of Candida albicans populations in the mouths of complete denture wearers, Microbiologica, 21, pp. 41-48 (1998).
Aoba, T., et al., Dental Fluorosis: Chemistry and Biology, Critical Reviews in Oral Biology & Medicine, 13, pp. 155-170 (2002).
Bagg J., et al., Voriconazole susceptibility of yeasts isolated from the mouths of patients with advanced cancer. Journal of Medical Microbiology, 54, pp. 959-964 (2005).
Barkvoll et al., Interaction Between Chlorhexidine Digluconate and Sodium Monofluorophosphate in Vitro, Scand. J. Dent. Res., 96(1), abstract (1 page) (1988).
Benarde et al., Kinetics and Mechanism of Bacterial Disinfection by Chlorine Dioxide, Applied Microbiology, vol. 15, No. 2, pp. 257-265 (1967).
Berg J.D., et al.., Effect of chlorine dioxide on selected membrane functions of *Escherichia coli*, Journal of Applied Bacteriology, 60, pp. 213-220 (1986).
Blignaut, E., Oral candidiasis and oral yeast carnage among institutionalized South African paediatric HIV/AIDS patients, Mycopathologia, 163, pp. 67-73 (2007).
Bouillaguet S., Biological Risks of Resin-Based Materials to the Dentin-Pulp Complex, Critical Reviews in OralBiology & Medicine,15(1), pp. 47-60 (2004).
Braly A. et al., The Effect of Prism Orientation in the Indentation Testing of Human Molar Enamel, Arch. Oral Biol., 52(9), pp. 856-860 (2007).
Brand H.S., et al., Effect of a protein-rich meal on urinary and 2 salivary free amino acid concentrations in human subjects, Clinica Chimica Acta, 264; 37-47, abstract (1 page) (1997).
Campisi G., et al., Candidal carriage in the oral cavity of human immunodeficiency virus-infected subjects, Oral Surgery Oral Medicine Oral Pathology Oral Radiology and Endodontics, 93, pp. 281-286 (2002).
Canton E., et al., Minimum fungicidal concentrations of amphotericin B for bloodstream *Candida* species, Diagnostic Microbiology and Infectious Disease, 45, pp. 203-206 (2003).
Cartledge M.D., et al., Non-albicans oral candidiasis in HIV-positive patients, Journal of Antimicrobial Chemotherapy, 43, pp. 419-422 (1999).
Cate, et al., Molecular and Cellular Mechanisms That Lead to Candida Biofilm Formation, J Dental Research, 88 (2), pp. 105-115 (2009).
Challacombe S.J., Immunologic aspects of oral candidiasis, Oral Surgery Oral Medicine Oral Pathology, 78, pp. 202-210 (1994).
Chang H., et al., High-resolution 1 H NMR investigations of the oxidative consumption of salivary biomolecules by oral rinse peroxides, Acta Odontologia Scandanivica (in press), abstract (1 page) (2012).
Chang H., et al., 1H NMR investigations of the molecular4 nature of cobalt(II) ions in human saliva, Archives of Biochemistry and Biophysics, 520, (Abstract) 1 page (2012).
Chapek, et al., Management of Periodontitis with Oral-Care Products, Compend. Cantin. Educ Dent, vol. XV, No. 6, 4 pgs (1994).
Masschelein W.J., Chlorine Dioxide: Chemistry and Environmental Impact of Oxychlorine Compounds, AnnArbor Science Publishers Inc., Ann Arbor, Michigan, p. 138-141 (1979).
McCarthy G.M., et al., Factors associated with increased frequency of HIV-related oral candidiasis, Journal of Oral Pathology and Medicine, 20, pp. 332-336 (1991).

Mjor, I.A., Dentin Permeability: The Basis for Understanding Pulp Reactions and Adhesive Technology, Braz. Dent. J., 20(1), pp. 3-16 (2009).
Mohammad A.R., et al., Clinical and microbiological efficacy of chlorine dioxide in the management of chronic atrophic candidiasis: an open studY, International Dental Journal, 54(3), pp. 154-158 (2004).
Moran G.P., et al., Antifungal Drug Susceptibilities of Oral Candida dubliniensis Isolates from Human Immunodeficiency Virus (HIV)-Infected and Non-HIV-Infected Subjects and Generation of Stable Fluconazole-Resistant Derivative In Vitro., Antimicrobial Agents and Chemotherapy, 41(3), pp. 617-623 (1997).
Moran G.P., et al, Emergence of non-Candida albicans *Candida* species as pathogens, in R.A. Calderone (ed.), Candida and Candidaisis. Washington, DC: ASM Press, pp. 37-53 (2002).
Nguyen D.H., et al., Common Dental Infections in the Primary Care Setting, Am.Fam. Physician 77(6), pp. 197-802 (2008).
Ogaard, B, et al., Professional Topical Fluoride Applications—Clinical Efficacy and Mechanism of Action; Adv. Dent.Res. 8(2), pp. 190-201 (1994).
oxyfresh.com, "Flouride with Fresh Mint Mouthrinse," Oral Health Care, Oxyfresh Worldwide, Inc., http://web.archive.org/web/20061023030535/https://oxyfresh.com/dental/rinse_flouride.asp., 2 pages, (Oct. 23, 2006).
oxyfresh.com, "Flouride with Fresh Mint Mouthrinse," Oral Health Care, Oxyfresh Worldwide, Inc., http://web.archive.org/web/20080509170508/https://oxyfresh.com/dental/rinse_flouride_asp., 2 pages, (May 9, 2008).
oxyfresh.com, "Flouride Kit," Oral Health Care, Oxyfresh Worldwide, Inc., http://web.archive.org/web/20061023030354/https://oxyfresh.com/dental//ohkits_flouride . . . , 2 pages, (Oct. 23, 2007).
Pappas, et al., A Prospective Observational Study of Candidemia: Epidemiology, Therapy, and Influences on Mortality in Hospitalized Adult and Pediatric Patients, Clinical Infectious Diseases, 37, pp. 634-643 (2003).
Pashley D.H., Dynamics of the Pulpo-Dentin Complex; Critical Reviews in Oral Biology & Medicine, 7, pp. 104-133 (1996).
Pfaller, et al., Epidemiology of Invasive Candidiasis: a Persisitent Public Health Problem, Clinical Microbiolog Reviews, pp. 133-163 (Jan. 2007).
Redding, et al., Candida glabrata is an emerging cause of oropharyngeal candidiasis in patients receiving radiation for head and neck cancer, Oral Surgery Oral Medicine Oral Pathology Oral Radiology and Endodontics, 97, pp. 47-52 (2004).
Redding S.W., The role of yeasts other than Candida albicans in oropharyngeal candidiasis, Current Opinion in Infectious Diseases, 14, pp. 673-677 (2001).
Rees, et al., The Epidemiological Features of Invasive Mycotic Infections in the San Francisco Bay Area, 1992-1993: Results of Population-Based Laboratory Active Surveillance, Clinical Infectious Diseases, 27, pp. 1138-1147 (1998).
Rex, et al., Development of interpretive breakpoints for antifungal susceptibility testing: conceptual framework and analysis of in vitro—in vivo correlation data for fluconazole,itraconazole, and Candida infections, Subcommittee on Antifungal Susceptibility Testing of the National Committee for Clinical Laboratory Standards. Clinical Infectious Diseases,24(2), pp. 235-247 (Feb. 1997).
Rex J.H., et al. Practice guidelines for the treatment of candidiasis, Clinical Infectious Diseases, 30 (4), pp. 662-278 (2000).
Robinson C, et al., The Chemistry of Enamel Caries; Critical Reviews in Oral Biology & Medicine, 11 (4), pp. 481-495 (2000).
Roller S.D., et al., Mode of Bacterial Inactivation by Chlorine Dioxide, Water Research, 14, pp. 635-641 (1980).
Rose L.F., et al., Periodontics: Medicine, Surgery, and Implants, St. Louis: Mosby, Inc., pp. 20, 70, 847-848 and 354, (2004).
Samaranayake L.P., et al., Oral candidiasis and human immunodeficiency virus infection, Journal of Oral Pathology and Medicine, 18, pp. 554-564 (1989).
Samonis G, et al., Oropharyngeal candidiasis as a marker for esophageal candidiasis in patients with cancer, Clinical Infection Diseases, 27, pp. 283-286 (1998).
San-Blas et al., Fungal morphogensis and virulence, Medical Mycology, 38, pp. 79-86 (2000).

(56) References Cited

OTHER PUBLICATIONS

Sharma G, et al., Oral manifestations in HIV/AIDS infected patients from India, Oral Diseases, 12, pp. 537-542 (2006).
Shinada, et al., A randomized double blind crossover placebo-controlled clinical trial to assess the effects of a mouthwash containing chlorine dioxide on oral malodor, Trials, BioMed Central, London GB, vol. 9, No. 1, 8 pgs. (Dec. 9, 2008).
Silwood C.J.L., et al., A multifactorial investigation of the ability of oral health care products (OHCPs) to alleviate oral malodour, Journal of Clinical Periodontology, 28, pp. 634-641 (2001).
Slavinsky J, et al., Th1/Th2 cytokine profiles in saliva of HIV-positive smokers with oropharyngeal candidiasis, Oral Microbiology and Immunology, 17, pp. 38-43 (2002).
Soysa N.S., et al., The impact of cigarette/tobacco smoking on oral candidiasis: an overview, Oral Diseases, 11, pp. 268-273 (2005).
Spellberg, et al., Current Treatment Strategies for Disseminated Candidiasis, Clinical Infection Diseases, 42, pp. 244-251 (2006).
Stookey G.K., et al., Animal Caries Models for Evaluating Fluoride Dentifrices; Advances in Dental Res. 9(3);pp. 198-207 (1995).
Takasawa H, et al., An elderly case of Type 2 diabetes which developed in association with oral and esophageal candidiasis, Internal Medicine, 46(7), pp. 387-390 (2007).
Taylor G.W., et al., Special Review in Periodontal Medicine: Periodontal disease: associations with diabetes, glycemic control and complications, Oral Diseases 14, pp. 191-203 (2008).
The Proprietary Association Subgroup on Fluoride Dentifrices, Standards for FluorideDentifrices, 4 pgs (Mar. 11, 1978).
Thompson et al., Coevolution of Morphology and Virulence in *Candida* Species, Eukaryotic Cell, Vo. 10, No. 9, pp. 117-1182 (2011).
United States Environmental Protection Agency, Alternative Disinfectants and Oxidants Guidance Manual, 2 pgs (1999).
Vargas, K. et al., Carnage frequency, intensity of carriage, and strains of oral yeast species vary in the progression to oral candidiasis in human immunodeficiency virus-positive individuals, Journal of Clinical Microbiology 40(2), pp. 341-350, (2002).
Vazquez, J., Diagnosing and Managing Oropharyngeal candidiasis, Infections in Medicine 24, pp. 427-436, (2007).
Viale, P., Candida Colonization and Candiduria in Critically Ill Patients in the Intensive Care Unit, Drugs Suppl 1, 51-57, abstract (1 page) (2009).
Villhauer A, et al., Bactericidal Activity of Stabilized Chlorine Dioxide Against Polymicrobial Biofilms; International Assoc. for Dental Research Poster #3417, General Session, Apr. 1-4, 1 page (2009).
Wang L, et al., Mimicking the Self-Organized Microstructure of Tooth Enamel; J. Phys. Chem C Nanometer Interfaces112(15), 16 pgs (2008).
Warrick J.M., et al., Caries-Preventive Effects of Sodium and Amine Fluoride Dentifrices, Am. J.Dent, 12(1), pp. 9-13 (1999).
Wei, M.K, et al., Plasma membrane damage to Candida albicans caused by chlorine dioxide (CIO2), Letters in Applied Microbiology 47(2), pp. 67-73, (2008).
Whelton H., et al., The Use of Combinations of Caries Preventive Procedures; Jour. Dent. Educ., vol. 65, No. 10, pp. 1110-1113 (2001).
Whitten, Kenneth W, et al., General Chemistry (6th Ed) Fort Worth, TX, Saunders College Publishing/Hartcourt College Publishets, ISBN 978-0-03-072373-5, pp. 27-46 (2000).
Williams, et al., Isolation and identification of Candida from the oral cavity, Oral Disease, 6(1), 3-11 (Jan. 2000).
Willis A.M., et al., Oral candidal carriage and infection in insulin-treated diabetic patients, Diabetic Medicine, 16, pp. 675-679 (1999).
Wirthlin M.R., et al., Chlorine dioxide and water rinses in gingivitis, Rowpar Pharmaceuticals Study Report, OSAP Annual Symposium, 1 page, (2003).
Wirthlin M.R., et al., Formation and Decontamination of Biofilms in Dental Unit Waterlines; J. Periodontol, 74 (11), pp. 1595-1609 (2001).
Chattopadhyay A., et al., Risk indicators for HIV-associated jointly occurring oral Candidiasis and oral hairy leukoplakia, AIDS Patient Care and STDs, 21 (11 ), pp. 825-832 (2007).
Chattopadhyay A., et al. Risk indicators for oral candidiasis and oral leukoplakia in HIV-infected adults. Community Dentistry and Oral Epidemiology, 33, pp. 35-44 (2005).
Chattopadhyay A., et al. Incidence of oral candidiasis and oral hairy leukoplakia in HIV-infected adults in North Carolina, Oral Surgery Oral Medicine Oral Pathology Oral Radiology and Endodontics, 99, pp. 39-47 (2005).
Chinake, et al., Oxidation of formaldehyde by chlorite in basic and slightly acidic media. Journal of Physical Chemistry, vol. 102, pp. 606-611, (1998).
Chinake, et al., Oxyhalogen-Sulfur Chemistry: Oxidation of Taurine by Chlorite in Acidic Medium, Jounral of Physical Chemistry, 101, pp. 1207-1214 (1997).
CLSI, Reference Method for Broth Dilution Antifungal Susceptibility Testing of Yeasts; Approved Standard—Second11 Edition, CLSI document M27-A2 (ISBN 1-56238-469-4), CLSI, 940 West Valley Road, Suite 1400, Wayne, PA 19087-1898 USA, 15 pgs (2002).
Coleman et al., Candidiasis: the emergence of a novel species, *Candida dubliniensis*, AIDS, vol. 11, No. 5, pp. 557-567, (1997).
Conley L.J., et al., The association between cigarette smoking and selected HIV-related medical conditions, AIDS, 10, pp. 1121-1126 (1996).
Coogan, et al., (B1) Candida and Mycotic Infections, Advances in Dental Research, No. 19, pp. 130-138 (2006).
Cury J. et al., Enamel Remineralization: Controlling the Caries Disease or Treating Early Caries Lesions?, Braz. OralRes., 23 Spec.Issue 1; pp. 23-30 (2009).
Cury J. et al., How to Maintain a Cariostatic Fluoride Concentration in the Oral Environment, Advances in DentalRes., 20; pp. 13-16 (2008).
Darkwa, et al., Oxyhalogen-Sulfur Chemistry: Oxidation of N-Acetylcysteine by Chlorite and Acidic Bromate, The Journal of Physical Chemistry A., vol. 107, No. 46, pp. 9834-9845 (Nov. 1, 2003).
Davies A.N., et al., Oral candidosis in patients with advanced cancer, Oral Oncology, 42, pp. 698-702 (2006).
Denes, G. et al., Oxidation of SnF2 Stannous Fluoride in Aqueous Solutions, Hyperfine Interactions, vol. 90,No. 1, 2 pgs (1994).
Edgar W.M., et al., Role of Saliva in Caries Models, Advances in Dental Res., 9(3); pp. 235-238 (1995).
Emilson, C.G., et al., Effect of a Fluoride-Containing Chlorhexidine Gel on Bacteria in Human Plaque, Scand.J. Dent. Res., 84(2), abstract (1 page) (1976).
European Commission, Enterprise Directorate-General, The Rules Governing Cosmetic Products in the European Union,Cosmetics Legislation,—Cosmetic products, 1999 Edition, vol. 1, 3 pgs (1999).
Featherstone, J.D.B., Caries Prevention and Reversal Based on the Caries Balance, Pediatric Dentistry, 28(2); pp. 128-132 (2006).
Featherstone, J.D.B., Delivery Challenges for Fluoride, Chlorhexidine and Xylitol, BMC Oral Health; 6:S8, 5 pgs (2006).
Final Report: Study No. 1439, The Effect of Experimental Oral Care Products on Caries Formation in the Rat (similar to FDA #37), 18 pgs (2008).
Final Report: EFU-R-0701, Fluoride Uptake in Incipient Enamel Lesions After Dentifrice Treatment (FDA Test #40, pgs (2007).
Food and Drug Administration, Anticaries Drug Products for Over-the-Counter Human Use: Final Monograph, Title 21, Federal Register, vol. 60, No. 194, Parts 310, 355, and 369, 2 pgs (1995).
Food and Drug Administration, US Dept of Health and Human Services; Guidance for Industry Q1A(R2) Stability Testing of New Drug Substances and Products, Rev. 2, 25 pgs (Nov. 2003).
Freitas, C., et al., Evaluation of the Substantivity of Chlorhexidine in Association with Sodium Fluoride in Vitro, Pesqui Odontol Bras, 17(1), pp. 78-81 (2003).
Garcia-Godoy F, et al, Maintaining Integrity of the Enamel Surface: The Role of Dental Biofilm, Saliva, and Preventive Agents in Enamel Demineralization and Remineralization; Jour.Am.Dent. Assoc. ,139; pp. 25S-34S (2008).

(56) References Cited

OTHER PUBLICATIONS

Goncalves R.H.P., et al., Species diversity of yeast in oral colonization of insulin-treated diabetes mellitus patients, Mycopathologia, 162, pp. 83-89 (2006).
Gonzalez-Gravina, et al., Oral candidiasis in children and adolescents with cancer, Identification of *Candida* spp, Medicina Oral, Patologia Oral y Cirugia Bucal, 12(6), pp. E419-423 (2007).
Grootveld, M., et al., Evidence for the Microbicidal Activity of a Chlorine Dioxide-Containing Oral Rinse Formulation in Vivo, J.Clin. Dentistry, vol. XII(3), pp. 67-70 (2001).
Gudlauggson, et al., Attributable mortality of nosocomial candidemia, revisited, Clin. Infect. Dis. 37, pp. 1172-1177 (2003).
Gunsolley J.C., A Meta-Analysis of Six-Month Studies of Antiplaque and Antigingivitis Agents, Jour.Am.Dent. Assoc, 137; pp. 1649-1657 (2006).
Hajjeh, et al., Incidence of bloodstream infections due to *Candida* species and in vitro susceptibilities of isolates collected from 1998 to 2000 in a population-based active surveillance program, Journal of Clinical Microbiology, col. 42, No. 4, pp. 1519-1527 (2004).
Harakeh S, et al., Inactivation of Bacteria by Purogene, J.Appl. Bacteriol, 64(5), abstract (1 page) (1988).
Hazen S.L., et al., Human neutrophils employ the myeloperoxidase-hydrogen peroxide-chloride system to oxidize alpha-amino acids to a family of reactive aldehydes, Mechanistic studies identifying labile intermediates along the reaction pathway, J Biol Chem., 273(9), pp. 4997-5005 (Feb. 27, 1998).
International Conference on Harmonisation of Technical Requirements for Registration of Pharmaceuticals for Human Use (ICH), Guidance for Industry Q1A(R2) Stability Testing of New Drug Substances and Products, 24 pgs (2003).
Islam B, et al., Dental Caries: From Infection to Prevention, Med.Sci.Monit, 13(11): pp. RA196-RA203 (2007).
Jacobsen, et al., Mixed Candida albicans strain populatins in colonized and infected mucosal tissues, Federation of European Microbiological Societies Yeast Res 8, pp. 1334-1338, (2008).
Keyes, P.H., Dental Caries in the Molar Teeth of Rats: II. A Method for Diagnosing and Scoring Several Types of Lesions Simultaneously, Jour. of Dent. Res. 17(6), pp. 1088-1099 (1958).
Kidd E.A.M., et al. What Constitutes Dental Caries? Histopathology of Carious Enamel and Dentin Related to the Action of Cariogenic Biofilms, Jour. of Dent. Res., 83; pp. C35-C38 (2004).
Kirsch, Final Report—The evaluation of chlorine dioxide dentifrice formulations, University of Iowa, pp. 1-90, (2006).
Kleinberg et al., The pH of Dental Plaques in the Different Areas of the Mouth Before and After Meals and their Relationship to the pH and Rate of the Flow of Resting Saliva, Archives of Oral Biology, vol. 9, pp. 493-516, (1964).
Kolahi J, et al., Rinsing With Chlorhexidine Gluconate Solution After Brushing and Flossing Teeth: A Systematic Review of Effectiveness; Quintessence Int., 37(8), abstract (1 page) (2006).
Krishnaraju R.K., et al., Comparative Genomics and Structure Prediction of Dental Matrix Proteins, Advances InDental Res., 17; pp. 100-103 (2003).
Lendennman U, et al., Saliva and Dental Pellicle—A Review, Advances in Dental Res., 14; pp. 22-28 (2000).
Leone C.W., et al., Physical and Chemical Aspects of Saliva as Indicators of Risk for Dental Caries in Humans, Jour.Dent. Educ., vol. 65, No. 10, pp. 1054-1062 (2001).
Li L, et al., Candida glabrata, an emerging oral opportunistic pathogen, Journal of Dental Research, 86(3), pp. 204-215 (2007).
Lockhart S.R., et al. Natural defenses against Candida colonization breakdown in the oral cavities of the elderly, Journal of Dental Research, 78, pp. 857-868 (1999).
Luoma H, et al., A Simultaneous Reduction of Caries and Gingivitis in a Group of Schoolchildren ReceivingChlorhexidine-Fluoride Applications, Results After 2 Years; Caries Res., 12, 2 pages (1978).
Lynch, E, et al., Multicomponent Spectroscopic Investigations of Salivary Antioxidant Consumption by an Oral Rinse Preparation Containing the Stable Free Radical Species Chlorine Dioxide (ClO2); Free Radical Research, 26(3), pp. 209-234 (Mar. 1997).
Margolis H.C., et al., Role of Macromolecular Assembly of Enamel Matrix Proteins in Enamel Formation, Jour. of Dent. Res., 85, pp. 775-793 (2006).
Masschelein W.J., Chlorine Dioxide: Chemistry and Environmental Impact of Oxychlorine Compounds, AnnArbor Science Publishers Inc., Ann Arbor, Michigan, pp. 153-156 (1979).
American Dental Association, "Fluoridation Facts," 72 Pages, (2005 Edition).
Pushalkar et al., "Oral Microbiota and Host Innate Immune Response in Bisphosphonate-Related Osteonecrosis of the Jaw," International Journal of Oral Science, vol. 6, pp. 219-226, (2014).
Rosella et al, "Medication-Related Osteonecrosis of the Jaw: Clinical and Practical Guidelines," Journal of International Society of Preventive & Community Dentistry, vol. 6(2), pp. 97-104, (2016).
Non-Final Office Action dated Dec. 21, 2018 in U.S. Appl. No. 13/131,506.
Requirement for Restriction dated Dec. 26, 2018 in U.S. Appl. No. 16/133,359.
PCT; International Search Report dated Nov. 30, 2018 in International Application No. PCT/US2018/049302.
PCT; Written Opinion dated Nov. 30, 2018 in International Application No. PCT/US2018/049302.
Brennan, "Examples of Acidic Buffers," Examples of Acid Buffering, Sciencing, https://sciencing.com/examples-acidic-buffers-6926552.htm, 3 Pages, (Apr. 25, 2018).
USPTO; Non-Final Office Action dated Mar. 8, 2019 in U.S. Appl. No. 11/774,730.
EPO; Extended European Search Report dated Jan. 20, 2020 for European Application No. 18785801.4; 9 pp.

\* cited by examiner

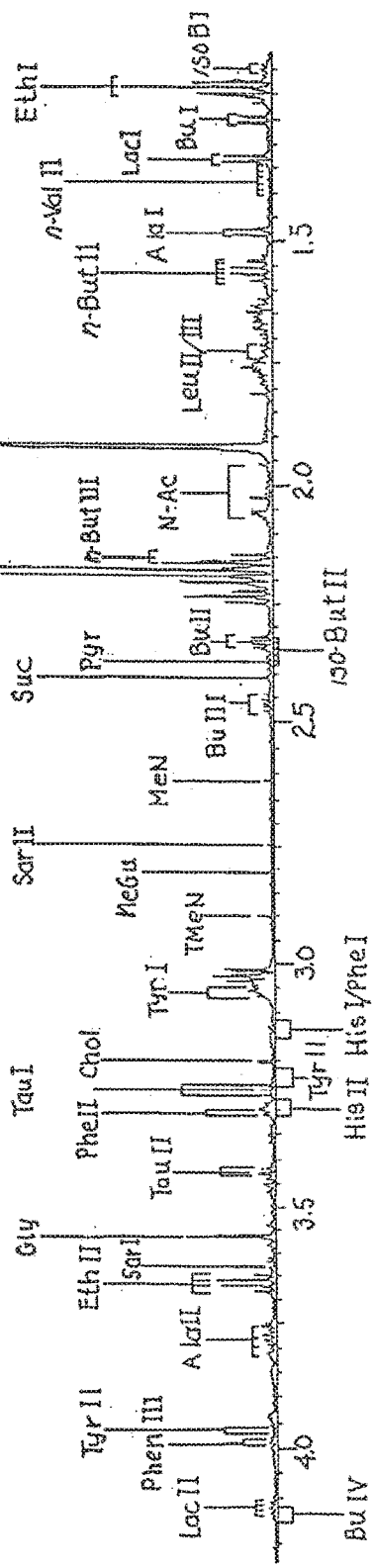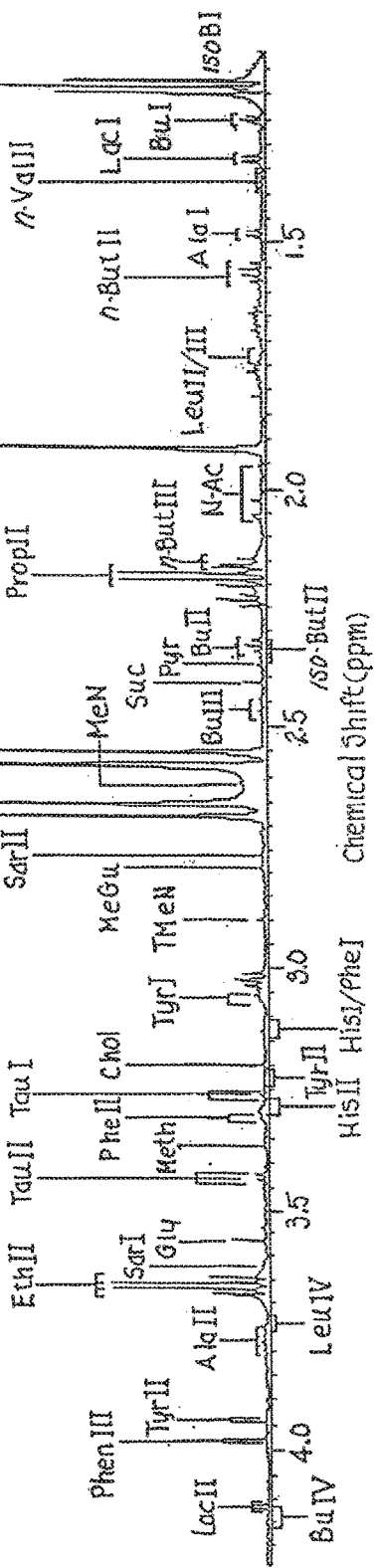
Fig.1a.
Fig.1b.

COMPOSITION AND METHOD FOR THE GENERATION OF CHLORINE DIOXIDE FROM THE OXIDATIVE CONSUMPTION OF BIOMOLECULES

CROSS REFERENCE TO RELATED APPLICATIONS

The present application is a continuation of, claims priority to and the benefit of U.S. Ser. No. 12/704,360 filed Feb. 11, 2010 and entitled "Composition and Method for the Generation of Chlorine Dioxide from the Oxidative Consumption of Biomolecules." The '360 application includes subject matter disclosed in and claims priority to a U.S. Provisional Patent Application No. 61/152,336 filed Feb. 13, 2009 and entitled "Oxidative Consumption of Salivary Biomolecules," assigned to the present assignee. Both of the aforementioned applications are incorporated herein by reference in their entirety.

FIELD OF THE INVENTION

The present invention relates to the oxidative consumption of salivary biomolecules, in particular, it relates to the generation of chlorine dioxide for antibacterial affects in the oral cavity with a stabilized chlorine dioxide composition.

BACKGROUND OF INVENTION

Oral disease refers to a number of generally preventable conditions of the mouth with a variety of causes. Plaque is the most recognizable precursor to oral disease. It is the biofilm that forms on teeth within hours after they are cleaned. The main mineral component of teeth is hydroxyapatite (HAP) and when teeth are cleaned, HAP becomes exposed to the oral environment. Salivary proteins such as mucins, proline-rich proteins, statherins, histatins, and cystatins have a strong affinity for HAP. These proteins quickly bind or adsorb to the exposed HAP of the tooth to form a thin coating called the acquired pellicle. Certain bacteria in the oral cavity selectively adhere to the pellicle, begin to divide, and form colonies. Initially, approximately 80% of the bacteria that colonize pellicle-coated tooth surfaces are facultative, gram-positive, non-motile cocci such as *Streptococcus sanguinis* (formerly *Streptococcus sanguis*). The other 20% include a variety of gram-negative bacteria such as *Veillonella* species. As the colonies grow, the environment changes due to the metabolic activities of these early colonizers and the addition of diverse groups of other bacteria to the biofilm (plaque) mass. An important environmental change in the plaque biofilm is the low-oxygen environment that promotes colonization and growth of anaerobic bacteria. Microorganisms in the biofilm synthesize a slime matrix or glycocalyx from the abundant polysaccharides, glycoproteins, and dietary sugars (e.g., sucrose) present in the oral environment. Eventually, the plaque becomes a characteristic biofilm with a highly structured, matrix-embedded, diverse microbial population in which gene expression is severely altered. The volume and structure of the biofilm created provides protection to the bacteria housed within it, potentially reducing the efficacy of antimicrobials. As a result, disruption of the biofilm of plaque is typically accomplished by mechanical means (e.g., brushing, flossing, professional tooth cleaning). Use of certain anti-plaque and antiseptic agents has been suggested for prevention of biofilms, but these treatments are typically tested in vitro using pure strains of microbes cultured on agar. Such in vitro conditions do not adequately simulate the biofilm environment, which may limit the significance of the test results.

Within biofilms, continuous metabolic activity of bacteria produces acids that can demineralize tooth enamel and dentin leading to the development of dental caries and progressive tooth decay. This demineralization is irreversible unless there is early intervention by a dental professional who might recommend the inclusion of certain fluoride-containing oral care products in the daily dental routine. If left untouched, demineralization can progress to the inner layers of the tooth, leading to severe pain and increased potential for loss of the tooth.

If dental plaque is left undisturbed, deeper portions of the plaque biofilm mineralize leading to the formation of calculus. Calculus has two major components, organic material and inorganic material. The organic portion of calculus consists mainly of dead bacteria. The inorganic part of calculus is composed of several minerals derived from calcium and phosphate present in the oral environment. There are two types of calculus, subgingival (below the gum line) and supragingival (above the gum line). Supragingival calculus is highly organized, porous, and visible. Once formed, calculus cannot be removed by conventional brushing and flossing; the intervention of a dental professional is generally required. Calculus retention is problematic for oral health because it harbors biofilm-forming bacteria that can lead to the development of periodontal (gum) infections.

Halitosis (bad breath) is caused primarily by the presence of volatile sulfur compounds (VSCs) in expired breath. Approximately 90% of foul odors in expired mouth air are due to the presence of the two major VSCs: hydrogen sulfide ($H_2S$) and methyl mercaptan ($CH_3SH$— also called methanethiol). The sulfur in these VSCs comes from the breakdown by bacteria of sulfur-containing proteins from saliva, plaque, and sloughed epithelial cells. Increased production or build-up of any of the protein sources will lead to higher levels of VSCs in mouth air.

There are a number of known situations that will lead to increased VSC production. For example, persons who do not perform adequate oral hygiene will have abundant amounts of supragingival and subgingival plaque biofilms on their teeth. This is especially true in difficult-to-clean locations such as interproximal areas between the teeth. In addition, natural teeth that support some dental prostheses are difficult to clean. Finally, the dorsal surface of the tongue is rough, irregular, and harbors large quantities of microorganisms. In general, the microorganisms in chronic intraoral biofilms will produce large quantities of VSCs. Besides being the major contributor to halitosis, VSCs are potent irritants and can aggravate existing inflammation of the gums. High levels of VSCs can kill epithelial cells that may lead to increased permeability and ulceration of the gum tissue. The existence of open wounds coupled with increased gum tissue permeability can promote the entry of bacteria into the bloodstream (i.e., bacteremia). Chronic bacteremia may increase the risk for the development of a numbers of systemic problems such as heart attacks, stroke, and adverse birth outcomes.

Gingivitis is defined as the presence of gingival inflammation without loss of connective tissue attachment. The precursor to gingivitis is undisturbed dental plaque biofilms. Studies have shown that gingivitis will develop within 10-21 days if all oral hygiene practices are stopped and plaque is allowed to accumulate undisturbed. Clinical signs of gingivitis are redness, swelling (edema), and bleeding gums.

Periodontitis refers to a group of infections in which the supporting tissues of the teeth such as connective tissue and bone are destroyed by plaque-induced inflammation. The most common form is known as Chronic Periodontitis that affects approximately 20% of the adult U.S. population. Signs of chronic periodontitis include all of those associated with gingivitis (i.e., redness, swelling, bleeding) plus the formation of deep periodontal pockets (increased probing depths), gingival recession, increased tooth mobility, and loss of bone as detected by radiographs. If left untreated, chronic periodontitis can lead to tooth loss.

Several dozen types of oral bacteria have been implicated as putative periodontal pathogens including gram-negative bacteria such as: *Porphyromonas gingivalis, Aggregatibacter actinomycetemcomitans, Tannerella forsythia, Eikenella corrodens, Prevotella intermedia*, and *Campylobacter rectus*. Gram-positive bacteria of importance include *Streptococcus intermedius, Micromonas micros*, and *Eubacterium* species. Spirochetes such as *Treponema denticola* are also important. Low levels of most of these pathogens can be isolated from healthy mouths. These bacteria only become a problem when they are left undisturbed in mature dental plaque biofilms. Finally, chronic periodontitis is a polymicrobial infection with multiple bacteria working together in a biofilm to cause the disease.

Treatment of both gingivitis and chronic periodontitis is designed to facilitate the frequent removal and disruption of dental plaque biofilms. For gingivitis, effective oral hygiene practices on a daily basis are usually sufficient. This involves thorough removal of plaque from facial and lingual surfaces of the teeth with a toothbrush and good interproximal care with dental floss or other appropriate devices (e.g., toothpicks). Periodic tooth cleaning by an oral health care provider is required to remove mineralized plaque (i.e., calculus). Treatment of chronic periodontitis is more difficult since the disease-causing plaque is usually at subgingival sites and in deep periodontal pockets. Standard interventions usually include oral hygiene instructions followed by thorough subgingival debridement (i.e., scaling and root planing). If the infection persists, surgical intervention may be recommended to reduce the depth of the pockets and to gain access to thoroughly remove the calculus deposits on root surfaces. In some cases, reconstructive surgical procedures are performed in an attempt to regain some of the lost periodontal attachment and supporting bone. Once the infection is under control, the patient is placed on a rigorous maintenance/recall program to reduce the chances of recurrent infection. It is during this maintenance phase of therapy that non-invasive over-the-counter products are especially useful in slowing down the reformation of dental plaque biofilms on tooth surfaces.

Chlorine Dioxide

The use of chlorine dioxide for sanitation was first suggested in 1948 by Eric Woodward to reduce the incidence of unpleasant taste in shrimp. Since then, chlorine dioxide use has spread into a number of other industries. The oxidative power of $ClO_2$ is used in the manufacture of wood pulp as an agent for the bleaching of cellulose fibers. In water treatment, $ClO_2$ has become widely used for water sanitation. In this case, it has been shown to be effective at reducing the bacterial content, algae content, and odor associated with wastewater treatment. Additionally, the utilization of $ClO_2$ for treating drinking water has been effective without adversely affecting its taste. The benefits of $ClO_2$ over other processes utilizing ozone or bleach for example, are reduced cost, reduced toxicity and reduced production of chlorinated by-products.

In 1999 the EPA published "Alternative Disinfectants and Oxidants Guidance Manual," describing disinfectant uses for $ClO_2$ and containing information on the mechanism of generation, application and standards and regulations governing use of $ClO_2$ and other disinfectants. Major applications listed by table 4-5, section 4.8.2 in the manual are as follows: primary or secondary disinfectant, taste control, odor control, TTHM/HAA reduction (total trihalomethanes are chlorinated organics, chloroform [$CHCl_3$] and dichlorobromomethane [$CHCl_2Br$] for example; haloacetic acids are created when an atom from the halogen group, chlorine, for example, replaces a hydrogen on the acetic acid molecule), Fe and Mn control, color removal, sulfide destruction, phenol destruction and Zebra mussel control [EPA 1999, p. 4-34]. These are accomplished by oxidation of various substances found in water. For example, unpleasant tastes and odors (sulfides, phenols, others) can exist in water due to vegetative decay and algae content. $ClO_2$ reduces these tastes either by eliminating the source (algae) or oxidizing the causative taste and odor molecules. In the control of iron and manganese, $ClO_2$ will bring the dissolved ions out of solution to form precipitates, which may be eliminated through filtration and/or sedimentation. Zebra mussel control is important because it helps to maintain the natural ecology of a body of water. Zebra mussels are organisms that will infest a lake or river, strip it of nutrients and create a pseudo-fecal mucous layer on the bottom. The use of $ClO_2$ for water sanitation and pulp treatment generally involves on-site generation followed by immediate use.

The term 'stabilized chlorine dioxide' on the other hand, refers to the generation and subsequent sequestration of $ClO_2$, which allows for its storage and availability for later use. The first reference to stabilized chlorine dioxide in patent was in U.S. Pat. No. 2,482,891 in which $ClO_2$ is stabilized in a powder for storage. For its application, it is mixed with water to "liberate" the chlorine dioxide. A method and composition for the use of aqueous stabilized chlorine dioxide for antiseptic purposes was noted in U.S. Pat. No. 3,271,242. The 1979 text Chlorine Dioxide, Chemistry and Environmental Impact of Oxychlorine Compounds, describes (aqueous) stabilized chlorine dioxide as follows:

"The stabilization of chlorine dioxide in aqueous solution was proposed by using perborates and percarbonates. Thus, a stabilized solution of $ClO_2$ would be obtained at pH 6 to 8 by passing gaseous $ClO_2$ into an aqueous solution containing 12% $Na_2CO_3 \cdot 3H_2O_2$. Other variants are possible. In reality, it seems that in these methods, the chlorine dioxide is practically completely transformed to chlorite. Dioxide is released upon acidification . . . " [Masschelein, 1979]

The reference to percarbonates and perborates may be replaced by the term 'peroxy compounds,' which would refer to any buffer suitable for maintaining the pH and hence, the stability of the $ClO_2$ in solution. The buffer is a necessary component, as the $ClO_2$ is unstable at low pH. Once the solution reaches low pH or encounters an area of low pH, the stabilized $ClO_2$ is released from solution and available for sanitation and oxidation.

In oral care products, the use of stabilized $ClO_2$ has been suggested as an active ingredient by a number of patents: U.S. Pat. Nos. 4,689,215; 4,696,811; 4,786,492; 4,788,053; 4,792,442; 4,793,989; 4,808,389; 4,818,519; 4,837,009; 4,851,213; 4,855,135; 4,886,657; 4,889,714; 4,925,656; 4,975,285; 5,200,171; 5,348,734; 5,489,435; 5,618,550. Additionally, the use of stabilized $ClO_2$ has been suggested for the degradation of amino acids in U.S. Pat. No. 6,136, 348. The premise for these products is that the stabilized chlorine dioxide will remain as such until it encounters the localized reductions in pH. Reduced pH levels can be a result of low pH saliva or oral mucosa, the accumulation of oral disease-causing bacteria or the presence of plaque biofilms on teeth and epithelial cells. Once released, the now active chlorine dioxide is effective at killing bacteria and oxidizing VSCs. Data have shown dramatic reduction in bacteria after exposures as short as 10 seconds, as set forth in U.S. Pat. No. 4,689,215. Additional data show remarkable decrease in VSCs in expired mouth air; the mechanism is believed to be oxidation of VSCs through the cleavage of the sulfide bonds.

The effectiveness of the chlorine dioxide is likely dependent on the amount of $ClO_2$ released from stabilized chlorine dioxide when the solution is acidified. The amount of $ClO_2$ released depends on the initial concentration of the solution, its pH, and the stabilizing buffer or agent used. It could follow that that the efficacy of the chlorine dioxide as an oral care product is dependent on the amount of $ClO_2$ released from the stabilized chlorine dioxide solution. As a result, it is imperative that accurate, precise measurements are taken so the concentration of stabilized $ClO_2$ and of the release of $ClO_2$ from solution can be determined. In addition to the need to quantify the efficacy of the solution, concentrations must be understood to ensure the safety of the product.

A concern about the stability of stabilized $ClO_2$ was recited in U.S. Pat. No. 5,738,840 with reference to the inclusion of "other oxychlorine species" which could refer to chloride [$Cl^-$] or chlorate [$ClO_3^-$]. The mechanism of action was questioned and suggested that at pH between 6.2 and 7.0 "any molecular chlorine dioxide which forms by degradation of the chlorite is converted back to chlorite by reaction with the residual stabilizer." This reverse reaction is unlikely due to the lower pH in the bacteria-laden target areas of the mouth described earlier. U.S. Pat. No. 6,231,830 calls into question the stoichiometry and safety of the formulation presented in U.S. Pat. No. 5,738,840. It is claimed that the formulation described is a 'chlorinator' in which " . . . a build-up of chlorate ion, an unwanted by-product" may occur.

PRIOR ART

Previous inventions contemplate the use of stabilized chloride dioxide as a bactericide for the treatment gingivitis as well as a deodorizing agent for the treatment of oral malodor (Ratcliff, U.S. Pat. No. 4,689,215; Madray, U.S. Pat. No. 6,231,830 B1; Richter, U.S. Pat. No. 5,738,840; Witt, U.S. Pat. No. 6,350,438 B1). There is a large amount of evidence that indicates chlorine dioxide has bactericidal properties and that the chlorine dioxide serves to attack malodorous volatile sulfur compounds in the mouth by splitting of the sulfide bonds (Lynch et al., 1997; Silwood et al., 2001).

Grootveld et al. (2001) demonstrated that an admixture of oxohalogen oxidants chlorite and chlorine dioxide significantly reduces the number of *Streptococcus mutans* and lactobacilli. *Candida albicans* exhibited a decrease however not statistically significant. The research collected saliva samples from 33 dental patients prior to and following rinsing with the admixture oral rinse and measured the levels of each organism.

Research completed by Lynch et al. (1997) evaluated the oxidative consumption of salivary biomolecules by an oral rinse preparation containing an admixture of stable free radical species chlorine dioxide with chlorite anions. $^1$HNMR spectroscopy was used to obtain multicomponent evaluations of the actions of the oral rinse in the treatment of periodontal diseases and dental caries. Saliva samples were collected from 10 volunteers prior to and following rinsing and analyzed using the $^1$HNMR. Results indicated that the oxidative decarboxylation of salivary pyruvate and the oxidative consumption of urate, thiocyanate anion, and amino acids cysteine and methionine. The reductions in biomolecules included, but not limited to the following components: short-chain non-volatile carboxylic acid anions. The study revealed that the oral rinse composition of stable free radical species chlorine dioxide with chlorite anions reduces and removes pathogenic micro-organisms when used as an oral rinse.

Inventors, Ratcliff and Lynch, U.S. Pat. No. 6,136,348, suggest degradation of amino acids with the use of stabilized chlorine dioxide. The premise for the composition described in the patent is that stabilized chlorine dioxide is chlorine dioxide stabilized as a sodium chlorite at a neutral or alkaline pH. The composition will remain as such until it encounters the localized reductions in pH as in saliva. The formation of chlorine dioxide is a slow process and the effectiveness of the chlorine dioxide is likely dependent on the amount released from the stabilized chlorine dioxide. The patent describes the weak bonds between some amino acids, like cysteine, leading to susceptibility to being destroyed by oxidative consumption.

While prior art teaches various compositions of stabilized chlorine dioxide relative to oral health, they do not teach a method of stabilized chlorine dioxide to oxidatively consuming salivary biomolecules to produce antimicrobial affects for the reduction of growth and development of oral bacteria and microorganisms concerned with halitosis and oral disease by the generation of chlorine dioxide.

SUMMARY OF THE INVENTION

Stabilized chlorine dioxide has a beneficial effect of tending to prevent a number of factors of oral disease, both by eliminating the bacteria that cause them and also by oxidizing molecules associated with them using a solution in the form of a wash, rinse, soak, paste, gel, aerosol spray, or other suitable delivery system.

A buffered solution of aqueous sodium chlorite, when in solution at neutral to alkaline pH, is considered stabilized chlorine dioxide because it does not release the chlorine dioxide until it is acidified. It follows that measurement of the concentration of stabilized chlorine dioxide is not, in fact, a measurement of chlorine dioxide ($ClO_2$) contained in solution, but a quantification of the concentration of (aqueous) chlorite ($ClO_2-$) in solution. Once acidified, the amount of $ClO_2$ released is limited by and a direct result of the $ClO_2-$ concentration.

For liquids such as mouthwash, the standard unit of measurement when expressing concentration is weight-volume percentage. That is, a certain weight of component, solid, liquid, or dissolved in a solvent, is present in a certain volume of total mouthwash. Preferred concentrations of stabilized chlorine dioxide in this invention are in the range of 0.005% to 2.0% (w/v).

Halitosis is caused by the presence of volatile sulfur compounds. By which the sulfur compounds are produced from oral bacteria and other microorganisms, including fungi and virus forms, in the oral cavity and when undisturbed or not removed can lead to plaque and development of oral diseases, including gingivitis and periodontitis. Within the diverse ecology of the oral cavity and plaque are complex salivary biomolecules required for microorganisms to function, grow and develop. These salivary biomolecules act as building blocks for reproduction, increasing numbers of microorganisms and volatile sulfur compounds in the oral cavity leading to halitosis. By reducing or eliminating the presence of salivary biomolecules with stabilized chlorine dioxide, the growth and numbers of microorganisms in the oral cavity will be reduced or eliminated and therefore treating and preventing halitosis.

It is therefore a primary object of the present invention to provide stabilized chlorine dioxide as an antimicrobial agent against the oral microorganisms by generating chlorine dioxide by the oxidative consumption of salivary biomolecules.

Another object of the present invention is to provide stabilized chlorine dioxide as a halitosis treatment and prevention by the oxidative consumption and inactivation of volatile sulfur compounds and their amino acid precursors to alleviate halitosis.

Still another object of the present invention is to oxidatively consume and inactivate salivary biomolecules, including pyruvate, methionine, trimethylamine, tyrosine, glycine, creatine, 3-D-hydroxybutyrate, salivary taurine, lactate, and lysine.

Yet another object of the present invention is to provide stabilized chlorine dioxide composition in a solution or other delivery vehicle such as in the form of a wash, rinse, soak, paste, gel, or aerosol spray to deprive microorganisms of salivary biomolecules as necessary compounds to grow and develop.

A further object of the present invention is to prevent halitosis with stabilized chlorine dioxide composition by oxidatively consuming salivary biomolecules to eliminate and prevent microorganisms from growing and development in the oral cavity.

A still further object of the present invention is to treat halitosis with stabilized chlorine dioxide composition by oxidatively consuming salivary biomolecules to eliminate and prevent microorganisms from growth and development in the oral cavity.

Yet a further object of the present invention is to provide antimicrobial affects of stabilized chlorine dioxide on oral bacterial by producing chlorine dioxide as a product of oxidatively consuming salivary biomolecules.

These and other objects of the present invention will become apparent to those skilled in the art as the description thereof proceeds.

BRIEF DESCRIPTION OF FIGURES

FIG. 1, (a) and (b), illustrates the expanded 0.80-4.25 ppm regions of the 600.13 Mhz single-pulse $^1$H NMR spectra of a human salivary supernatant specimen (pH value 6.78) acquired (a) prior to and (b) subsequent to treatment with oral rinse I according to the procedure outlined in the Materials and Methods section. Abbreviations: A. Acetate-C$\underline{H}_3$; Ala I and II, alanine-C$\underline{H}_3$ and —C$\underline{H}$ group proton respectively; Bu I, β-hydroxybutyrate proton γ-C$\underline{H}_3$ group protons; Bu II, III and IV, β-hydroxybutyrate β, β', and α protons respectively (ABX coupling system); iso-But I and II, iso-butyrate-C$\underline{H}_3$ and —C$\underline{H}$ group protons respectively; n-But I, II and III, n-butyrate γ, β, and α protons respectively; Chol, choline-N$^+$ (C$\underline{H}_3$)$_3$; Cit, Citrate-AB-C$\underline{H}_2$—CO$_2^-$; DMeN, dimethylamine-C$\underline{H}_3$; Eth I and II, ethanol-C$\underline{H}_3$ and —C$\underline{H}_2$ group protons respectively; Form, formate-$\underline{H}$; Gly, glycine-C$\underline{H}$; His I and II, histidine ABX system β protons; Lac I and II, lactate-C$\underline{H}_3$ and —C$\underline{H}$ protons respectively; Leu I, II, III and IV, leucine δ, γ, β, and α protons respectively; MeGu, methylguanidine-C$\underline{H}_3$; MeN, methylamine-C$\underline{H}_3$; Meth, methanol-C$\underline{H}_3$; N—Ac, spectral region for acetamido methyl groups of N-acetyl sugars; Phe I and II, phenylalanine A$\underline{B}$X β protons; Prop I and II, propionate-C$\underline{H}_3$ and —C$\underline{H}_2$ group protons respectively; Pyr, pyruvate-C$\underline{H}_3$; Sar I and II, sarcosine-C$\underline{H}_3$ and —C$\underline{H}_2$ group protons respectively; Suc, succinate-C$\underline{H}_2$; Tau I and II, Taurine-C$\underline{H}_2$NH$_3^+$ and —C$\underline{H}_2$SO$_3^-$ protons respectively; TMeN, trimethylamine-C$\underline{H}_3$, Tyr I and II, tyrosine A$\underline{B}$X β protons; Tyr III, tyrosine AB$\underline{X}$ α proton; n-Val I and II, n-valerate δ and γ protons respectively.

DESCRIPTION OF THE INVENTION

Figure 2:
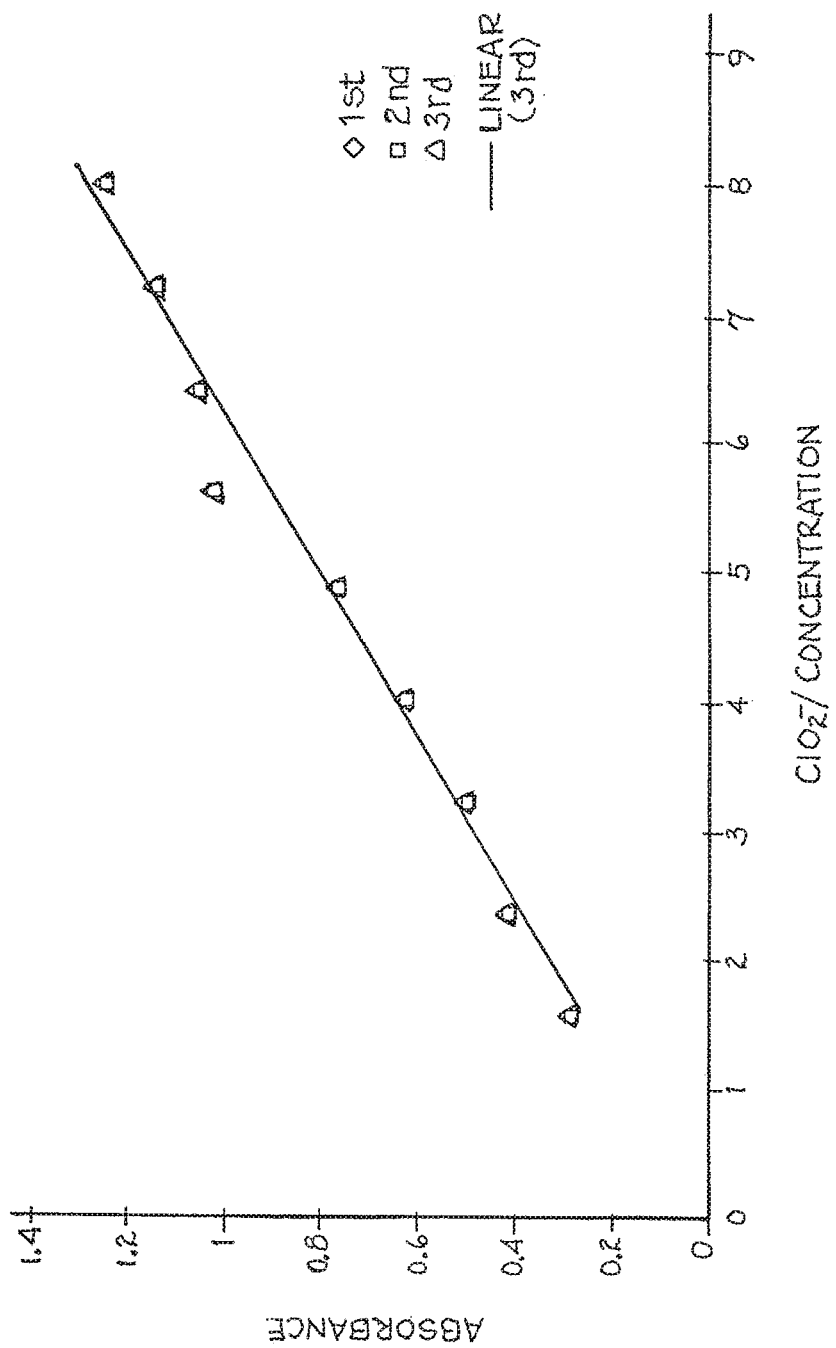
FIG. 2 illustrates a plot of absorbance at 262 nm (A$_{262}$) versus chlorite concentration for a series of calibration standards in the 1.60-8.00 mM concentration range

This invention relates to the discovery through research of the composition for and methodology of generating of chlorine dioxide by a stabilized chlorine dioxide composition through the oxidatively consuming salivary biomolecules in the oral cavity and producing antimicrobial affects on oral bacteria and microorganisms concerned with halitosis and oral disease with the reduction of growth and development. Chlorine dioxide is known to be a strong oxidizer and is capable of oxidizing amino acids. The work of Lynch et al. proves so with the degradation of cysteine and methionine into pyruvate in the presence of an admixture of stable free radical species chlorine dioxide with chlorite anions (1997). This was confirmed with the following evidence of research suggesting oxidative consumptions of salivary biomolecules and interactions of stabilized chlorine dioxide as chlorite with human salivary biomolecules. The oxidative decarboxylation of salivary pyruvate by stabilized chlorine dioxide composition indicates a mechanism of action of the interaction of this invention with salivary biomolecules as an antimicrobial agent.

The specific mechanism of action of 'stabilized' chlorine dioxide (specifically, chlorite anion) on oral organisms and biomolecules has not been fully investigated. The present invention research evidence suggests that stabilized chlorine dioxide oxidatively consumes salivary biomolecules and creates products that may exert bactericidal and bacteriostatic effects on the oral bacterial cells which ultimately gives rise to cell death. These effects can lead to control over the formation of bacterial plaque and the adverse generation of malodorous volatile sulfur compounds, major contributors to oral diseases.

The purpose of researching the oxidentive consumption of salivary biomolecules this investigation was to determine: (1) the metabolic profile of human saliva and the capacity of salivary biomolecules to react with stabilized chlorine dioxide oral rinse, (2) the amount of chlorine dioxide generated from chlorite when the oral rinse is mixed with saliva, and how much chlorine dioxide is consumed or chlorite remains, and (3) an assay technique for monitoring chlorine dioxide activity in saliva, as well as determining the level of volatile sulfur compounds after being treated with a stabilized chlorine dioxide rinse. The oral rinse compositions included a concentration of 0.1% (w/v) and 0.4% (w/v) stabilized chlorine dioxide. These formulations are designated as oral rinse I and II, respectively.

This research suggested that the stabilized chlorine dioxide composition has the capacity to clinically alleviate oral malodor by the direct oxidative inactivation of volatile sulfur compounds and their amino acid precursors. These results also reveal a new mechanism of action of stabilized chlorine dioxide (chlorite), specifically its reaction with human salivary biomolecules to produce chlorine dioxide.

Materials and Methods

Spectrophotometric Determination of Chlorite Concentrations in Oral Rinse Formulations For oral rinse I, 1.00 ml aliquots were diluted to a total volume of 3.00 ml with doubly-distilled water and electronic absorption spectra of these solutions were recorded on a Unicam UV-2 spectrophotometer in the 190-400 nm wavelength range. Similarly, 0.20 ml volumes of oral rinse II were diluted to a final volume of 3.00 ml with doubly-distilled water and electronic absorption spectra were also acquired in this manner. Chlorite concentrations were determined via measurement of its absorbance at 262 nm [$\varepsilon$=160 $M^{-1}$ $cm^{-1}$, as determined in this study]. A further series of these oral rinse solutions were pre-treated with the amino acid L-glycine (final concentration 2.00 mM) to remove hypochlorous acid/hypochlorite (HOCl/OCl$^-$) and chlorine dioxide (ClO$_2^\bullet$), the former generating glycine monochloroamine via equation A.

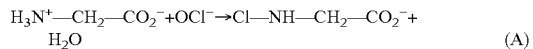

(A)

Results acquired revealed that there were no differences between spectra obtained before and after glycine treatment, indicating that these potentially interfering, further oxohalogen oxidants were absent from the oral rinse formulations examined.

Volunteer Recruitment and Collection of Samples

A series of non-medically-compromised volunteers (n=20) without any form of active periodontal disease or active dental caries were recruited to the study. To avoid interferences arising from the introduction of exogenous agents into the oral environment, volunteers were requested to collect all saliva available, i.e., ('whole' saliva expectorated from the mouth) into a plastic universal tube immediately after waking in the morning on a pre-selected day.

Each volunteer was also requested to refrain completely from oral activities (i.e., eating, drinking, tooth-brushing, oral rinsing, smoking, etc.) during the short period between awakening and sample collection (ca. 5 min.). Each collection tube contained sufficient sodium fluoride (15 µmol.) to ensure that metabolites are not generated or consumed via the actions of micro-organisms or their enzymes present in whole saliva during periods of sample preparation and/or storage.

Saliva specimens were transported to the laboratory on ice and then centrifuged immediately (3,000 r.p.m for 15 min.) on their arrival to remove cells and debris, and the resulting supernatants were stored at −70° C. for a maximum duration of 18 hr. prior to analysis. The pH values of each supernatant were determined prior to $^1$H NMR analysis.

Spectrophotometric Analysis of Residual (Unreacted) Chlorite Anion (ClO$_2^-$) in Oral Rinse/Salivary Supernatant Mixtures An ATI Unicam UV-VIS UV-2 spectrophotometer was employed for the determination of residual chlorite in each of the salivary supernatants collected in order to determine its level of consumption by biomolecules therein on equilibration.

0.09 ml aliquots of each salivary supernatant specimen were treated with 0.450 ml of oral rinse I. This mixture was thoroughly rotamixed and diluted to a final volume of 1.20 ml to yield an absorbance value of approximately 1 at 262 nm. The reference cell contained an equivalent volume of corresponding salivary supernatant diluted to a final volume of 1.20 ml with doubly-distilled H$_2$O. Initially, scans were made over the wavelength range of 190-300 nm.

Since oral rinse II contained exactly four times the concentration of ClO$_2^-$ [0.4% (w/v)], 0.10 ml aliquots of each salivary supernatant specimen were treated with 0.500 ml of this product, and once thoroughly rotamixed, a 0.135 ml aliquot of this mixture was diluted to a final volume of 1.20 ml with H$_2$O. The reference cell contained 22.5 µl of salivary supernatant diluted to 1.20 ml with H$_2$O.

ClO$_2^-$ has a wavelength of maximum absorbance ($\lambda_{max}$) at 262 nm ($\varepsilon$=160 $M^{-1}$ $cm^{-1}$) and therefore was readily detectable at the volumes (and hence concentrations of ClO$_2^-$) of each oral rinse added.

Where required, the pH value of samples were adjusted to a value of 1.00 and samples were then equilibrated at ambient temperature for a 24 hr. period (to ensure conversion of each mole of ClO$_2^-$ remaining to 0.50 of an equivalent of ClO$_2^\bullet$) in order to improve the sensitivity of this assay system [ClO$_2^\bullet$ has a $\lambda_{max}$ value in the visible region (360 nm) with $\varepsilon$=1,150 $M^{-1}$ $cm^{-1}$].

HPLC Monitoring of the Interaction of the Oral Rinse Oxohalogen Oxidants with Intact Human Saliva The chlorite level remaining in each salivary supernatant sample was also determined using a novel high-performance liquid chromatographic (HPLC) technique employing a reversed-phase C18 column with the ion-pair reagent hexadecyl-trimethylammonium bromide (HTB) present in the mobile phase. The operating system utilised was a Waters Millennium HPLC system, consisting of a Waters 626 Pump, Waters 996 Photodiode Array Detector and a Waters in-line degasser remotely operated using Waters unique Millennium software.

Samples were prepared via the treatment of 0.10 ml volumes of saliva supernatants with 0.50 ml aliquots of ¼ diluted oral rinses I and II. Once thoroughly rotamixed, 10 µl aliquots of the resulting solutions were injected using a remotely-operated automated auto-sampler with injector onto a reversed-phase C18 ODS Column (4.6×75 mm). A Spherisorb S5-ODS 1 guard column was employed to remove any potential analytical column contaminants.

The mobile phase was de-gassed using an in-line degasser. The mobile phase consisted of 2% (w/v) borate/gluconate buffer with 2% (v/v) butan-1-ol and 12% (v/v) acetonitrile (final pH 7.2) and operated at a flow rate of 1.10 ml/min. The ion-pair reagent (Hexadecyl-trimethylammonium Bromide) was added at a final concentration of 50.00 mM in order to ensure that ClO$_2^-$ is readily separated from interfering salivary components. This analyte was identified by comparisons of its peak's absorption spectrum generated by the photo-diode array detector ($\lambda_{max.}$ 262 nm) with that of an authentic chlorite standard.

Preparation of Human Salivary Supernatant Samples for $^1$H NMR Analysis

Each individual salivary supernatant sample was divided into three equivalent portions (0.60 ml). In total, there were three equivalent specimen reaction mixtures: 3.0 ml of oral rinses I and II were added to the first and second salivary supernatant samples respectively, whilst the third served as an untreated control in which 3.0 ml of $H_2O$ was added to the original 0.6 ml volume of salivary supernatant. The samples were then thoroughly rotamixed to ensure a homogenous mixture and then equilibrated at 37° C. for a period of 30 s.

Samples were prepared by adding 0.05 ml of deuterium oxide ($^2H_2O$, providing a field frequency lock) and 0.05 ml of a 5.0 mM solution of sodium 3-trimethylsilyl [2,2,3,3-$^2H_4$] propionate [TSP, chemical shift reference ($\delta$=0.00 ppm) and internal quantitative standard] in $^2H_2O$ to a 0.60 ml volume of each sample examined.

Each sample was then subjected to multicomponent high resolution $^1$H NMR analysis in order to identify the nature of salivary biomolecules which react with $ClO_2^-$ and/or $ClO_2^•$. i.e., via oxidative consumption or otherwise, together with the products generated from such reaction systems.

$^1$H NMR Measurements

One-dimensional (1-D) $^1$H NMR spectra were acquired on a Bruker AMX-600 spectrometer (ULIRS, Queen Mary, University of London facility, U.K) operating at a frequency of 600.13 MHz and a probe temperature of 298 K. The intense water signal ($\delta$=4.80 ppm) was suppressed by presaturation via gated decoupling during the delay between pulses.

Pulsing conditions for 1-D spectra acquired on salivary supernatant and oral rinse samples were: 128 free induction decays (FIDS); 16,384 data points; 3-7 μs pulses; 1.0 s pulse repetition rate. Line-broadening functions of 0.30 Hz were routinely utilised for the processing of experimental NMR data. Where present, the methyl group resonances of lactate ($\delta$=1.330 ppm) and alanine ($\delta$=1.481 ppm) served as secondary internal references for the control and oral rinse-treated salivary supernatant samples examined.

Results $^1$H NMR Analysis of Oral Rinse Formulations I and II $^1$H NMR spectra acquired on the oral rinse I formulation contained clear, prominent resonances ascribable to citrate [—C$\underline{H}_2$CO$_2^-$ protons, $\delta$=2.65 ppm (dd, AB coupling system)] which serves as a buffering agent, with lower intensity signals arising from acetate [—C$\underline{H}_3$ group, singlet (s) located at 1.92 ppm] and formate [$^-$O$_2$C—$\underline{H}$ singlet (s), $\delta$=8.46 ppm]. Ethanol [—C$\underline{H}_3$ and —C$\underline{H}_2$OH group protons, $\delta$=1.21(t) and 3.66(q) respectively] was also detectable at trace levels.

Spectra acquired on the oral rinse II product also contained resonances ascribable to citrate [—C$\underline{H}_2$CO$_2^-$ protons, $\delta$=2.65 ppm (dd, AB coupling system)] and lower intensity signals arising from trace levels of acetate [—C$\underline{H}_3$ group, singlet (s) located at 1.92 ppm] and formate [$^-$O$_2$C—$\underline{H}$ singlet (s), $\delta$=8.46 ppm].

$^1$H NMR Analysis of the Interaction of $ClO_2^-$-Containing Oral Rinse Formulations with Human Salivary Supernatant Specimens 600 MHz $^1$H NMR spectra were acquired for every salivary supernatant sample examined (i.e., a total of 60, 3 daily specimens collected from each of 20 human volunteers). A typical $^1$H NMR spectrum of a human salivary supernatant sample is shown in FIG. 2(a); that of the same saliva specimen pre-treated with Oral Rinse I is displayed in FIG. 2(b). These $^1$H NMR investigations [of the oxidative consumption of salivary biomolecules by oxohalogen oxidants present in Oral Rinses I and II tested (predominantly $ClO_2^-$)] revealed that:

1. Pyruvate was oxidatively decarboxylated to acetate and $CO_2$
2. The volatile sulphur compound (VSC) precursor methionine was oxidised to its corresponding sulphoxide
3. A resonance ascribable to malodorous trimethylamine (s, $\delta$=2.91 ppm) was reduced in intensity (a process presumably resulting in its transformation to trimethylamine oxide)
4. Tyrosine was oxidised (presumably to a quinone species)
5. The Glycine $\alpha$-CH$_2$ group resonance was reduced in intensity, an observation possibly attributable to its reaction with trace levels of hypochlorite/hypochlorous acid present in the oral rinses (generating mono- and/or dichloroamine species)
6. The concentrations of creatinine and 3-D-hydroxybutyrate were diminished following treatment with each oral rinse, an observation consistent with their oxidative consumption by oxohalogen species present therein.
7. Salivary taurine decreased in concentration post treatment.
8. Lactate-CH$_3$ and —CH signals were diminished in intensity following treatment.
9. Resonances ascribable to lysine were reduced in intensity post-treatment.

With regard to these $^1$H NMR analysis results acquired, the consumption of salivary methionine by chlorite is of much importance to oral hygiene and clinical periodontology since both CH$_3$SH and H$_2$S are generated from this amino acid via metabolic pathways operational in gram-negative micro-organisms. Hence, data acquired here indicates that the oral rinses examined have the capacity to clinically alleviate oral malodour via the direct oxidative inactivation of VSCs and their amino acid precursors.

As demonstrated here, the techniques employed are of much value concerning multicomponent assessments of the interactions of chlorite with human salivary biomolecules, and the oxidative decarboxylation of salivary pyruvate by this oxohalogen oxidant serves as an important example of this which may be of some relevance to its mechanisms of action.

Spectrophotometric Analysis of Chlorite Calibration Standards

Prior to spectrophotometric analysis of Oral Rinses I and II, the extinction coefficient of chlorite ($ClO_2^-$) was determined at its $\lambda_{max}$ value of 262 nm. This was conducted by analysing authentic $ClO_2^-$ calibration standards (1.60-8.00 mM, Table 1 and FIG. 2). Each measurement was made in triplicate in order to ensure the reproducibility of data acquired. Plots of absorbance at 262 nm ($A_{262}$) versus chlorite concentration were clearly linear: the extinction coefficient was determined as $\varepsilon$=160 M$^{-1}$ cm$^{-1}$, and the correlation coefficient (r) for the plot shown in Table 1 was 0.9955.

TABLE 1

Absorbance values at 262 nm for replicate (n = 3) determinations obtained for a series of chlorite calibration standards (1.60-8.00 mM)

| Concentration (mM) | 1st | 2nd | 3rd |
| --- | --- | --- | --- |
| 1.60 | 0.274 | 0.274 | 0.273 |
| 2.40 | 0.405 | 0.404 | 0.403 |
| 3.20 | 0.509 | 0.509 | 0.508 |

TABLE 1-continued

Absorbance values at 262 nm for replicate (n = 3) determinations obtained for a series of chlorite calibration standards (1.60-8.00 mM)

| Concentration (mM) | 1st | 2nd | 3rd |
|---|---|---|---|
| 4.00 | 0.632 | 0.63 | 0.631 |
| 4.80 | 0.784 | 0.783 | 0.783 |
| 5.60 | 1.032 | 1.034 | 1.033 |
| 6.40 | 1.055 | 1.056 | 1.055 |
| 7.20 | 1.161 | 1.163 | 1.161 |
| 8.00 | 1.253 | 1.252 | 1.252 |

Treatment of the water diluent with up to 20% (v/v) ethanol exerted no influence on the final absorbance values obtained, an observation which confirmed that this potential contaminant exerted no influence on the spectrophotometric assay of chlorite performed in this manner (i.e., no reaction between these agents was noted under our experimental conditions).

Spectrophotometric Determination of the Consumption of Oral Rinse Chlorite by Human Salivary Supernatant Specimens Following the establishment of $ClO_2^-$'s extinction coefficient (via the acquisition of electronic absorption spectra on a series of its calibration standards), difference spectrophotometric analysis of chlorite in each of the salivary supernatant/oral rinse mixtures was performed in order to determine its level of consumption by biomolecules therein on equilibration. In this manner, the decrease in absorbance at 262 nm observed following equilibration of the oral rinse formulations with human salivary supernatants according to the procedure outlined in methods was employed to estimate the level of oral rinse chlorite ($ClO_2^-$) consumption by this biofluid. Table 2(a) gives the concentrations of chlorite consumed (per ml of saliva) for reaction mixtures containing a 5:1 volume ratio of oral rinse:salivary supernatant.

TABLE 2(a)

Spectrophotometric determination of the consumption of oral rinse $ClO_2^-$ by human salivary supernatant samples (μmol. $ClO_2^-$ consumed per ml of saliva).

| Patient Code | Oral Rinse I | | | Oral Rinse II | | |
|---|---|---|---|---|---|---|
| J1 | 0.1640 | 0.1504 | 0.1776 | 0.0944 | 0.1168 | 0.1192 |
| J2 | 0.0200 | 0.0096 | 0.0176 | 0.0360 | 0.0280 | 0.0472 |
| J3 | 0.3040 | 0.3152 | 0.3040 | 0.3552 | 0.3024 | 0.3024 |
| BR1 | 0.0400 | 0.0760 | 0.0600 | 0.0696 | 0.0584 | 0.1136 |
| BR2 | 0.1136 | 0.0752 | 0.1008 | 0.1392 | 0.1136 | 0.1808 |
| BR3 | 0.2968 | 0.2800 | 0.3096 | 0.0976 | 0.0504 | 0.0776 |
| G1 | 0.0008 | 0.0104 | 0.0168 | 0.0584 | 0.1448 | 0.1168 |
| G2 | 0.0168 | 0.0080 | 0.0112 | 0.1528 | 0.1664 | 0.1640 |
| G3 | 0.0392 | 0.0624 | 0.0584 | 0.0864 | 0.0720 | 0.0920 |
| U1 | 0.0200 | 0.0112 | 0.0200 | 0.0528 | 0.0360 | 0.0248 |
| U2 | 0.0168 | 0.0040 | 0.0072 | 0.0168 | 0.0304 | 0.0392 |
| U3 | 0.0168 | 0.0216 | 0.0144 | 0.4504 | 0.3888 | 0.4056 |
| M1 | 0.0696 | 0.0728 | 0.0704 | 0.1000 | 0.1528 | 0.1280 |
| M2 | 0.0072 | 0.0016 | 0.0080 | 0.2024 | 0.1504 | 0.1608 |
| M3 | 0.0000 | 0.0048 | 0.0016 | 0.0192 | 0.0224 | 0.0224 |
| L1 | 0.0064 | 0.0040 | 0.0128 | 0.0248 | 0.0024 | 0.0112 |
| L2 | 0.0104 | 0.0064 | 0.0056 | 0.0416 | 0.0832 | 0.0696 |
| L3 | 0.0296 | 0.0320 | 0.0352 | 0.0664 | 0.064 | 0.0608 |
| SB1 | 0.1408 | 0.1576 | 0.1272 | 0.0720 | 0.0416 | 0.0664 |
| SB2 | 0.1400 | 0.1496 | 0.1336 | 0.2888 | 0.3584 | 0.2776 |
| SB3 | 0.0240 | 0.0240 | 0.0264 | 0.0224 | 0.0248 | 0.0336 |
| I1 | 0.0336 | 0.0424 | 0.0296 | 0.1112 | 0.1336 | 0.1528 |
| I2 | 0.0856 | 0.0752 | 0.0544 | 0.0448 | 0.0336 | 0.0248 |
| I3 | 0.0264 | 0.0216 | 0.0240 | 0.072 | 0.0976 | 0.0808 |
| R1 | 0.0376 | 0.0536 | 0.0368 | 0.0080 | 0.0224 | 0.0056 |
| R2 | 0.0056 | 0.0016 | 0.0000 | 0.1000 | 0.0752 | 0.0888 |

TABLE 2(a)-continued

Spectrophotometric determination of the consumption of oral rinse $ClO_2^-$ by human salivary supernatant samples (μmol. $ClO_2^-$ consumed per ml of saliva).

| Patient Code | Oral Rinse I | | | Oral Rinse II | | |
|---|---|---|---|---|---|---|
| R3 | 0.0056 | 0.0104 | 0.0104 | 0.0224 | 0.0112 | 0.0192 |
| ZK1 | 0.0088 | 0.0096 | 0.0096 | 0.0664 | 0.0552 | 0.0608 |
| ZK2 | 0.1032 | 0.1376 | 0.1248 | 0.0976 | 0.0752 | 0.1136 |
| ZK3 | 0.0232 | 0.0192 | 0.0264 | 0.1168 | 0.0808 | 0.0832 |
| V1 | 0.2000 | 0.2128 | 0.2264 | 1.4808 | 1.4888 | 1.4696 |
| V2 | 0.0328 | 0.0408 | 0.0472 | 0.2168 | 0.1552 | 0.1976 |
| V3 | 0.0704 | 0.0680 | 0.0672 | 0.7000 | 0.6528 | 0.6304 |
| Z1 | 0.0120 | 0.0096 | 0.0128 | 0.0664 | 0.0528 | 0.0552 |
| Z2 | 0.0240 | 0.0224 | 0.0184 | 0.0056 | 0.0024 | 0.0000 |
| Z3 | 0.0232 | 0.0184 | 0.0104 | 0.0504 | 0.0472 | 0.0552 |
| GG1 | 0.0344 | 0.0216 | 0.0328 | 0.2000 | 0.1752 | 0.1944 |
| GG2 | 0.1400 | 0.1296 | 0.1296 | 0.2392 | 0.2584 | 0.2472 |
| GG3 | 0.0088 | 0.0136 | 0.0104 | 0.0024 | 0.0136 | 0.008 |
| N1 | 0.0056 | 0.0064 | 0.0040 | 0.1976 | 0.2080 | 0.2000 |
| N2 | 0.0112 | 0.008 | 0.0048 | 0.0696 | 0.0752 | 0.0528 |
| N3 | 0.0184 | 0.0200 | 0.0120 | 0.0112 | 0.0168 | 0.0056 |
| ED1 | 0.0792 | 0.0576 | 0.0920 | 0.2752 | 0.2720 | 0.2448 |
| ED2 | 0.3184 | 0.3352 | 0.3288 | 0.3168 | 0.4640 | 0.4808 |
| ED3 | 0.0288 | 0.0224 | 0.0160 | 0.1080 | 0.1248 | 0.0608 |
| AB1 | 0.0112 | 0.0232 | 0.0256 | 0.2112 | 0.1608 | 0.1080 |
| AB2 | 0.0024 | 0.0032 | 0.0048 | 0.0584 | 0.1000 | 0.0944 |
| AB3 | 0.008 | 0.0104 | 0.0072 | 0.0552 | 0.0696 | 0.0696 |
| S1 | 0.2512 | 0.2736 | 0.2624 | 0.964 | 0.9832 | 1.0304 |
| S2 | 0.1952 | 0.1728 | 0.1584 | 0.1472 | 0.1696 | 0.1056 |
| S3 | 0.1176 | 0.1744 | 0.1440 | 0.5448 | 0.5776 | 0.5696 |
| DG1 | 0.1104 | 0.1144 | 0.0880 | 0.0504 | 0.0392 | 0.0664 |
| DG2 | 0.0192 | 0.0328 | 0.0208 | 0.0552 | 0.1360 | 0.0080 |
| DG3 | 0.0088 | 0.0120 | 0.0096 | 0.0808 | 0.0832 | 0.0888 |
| SG1 | 0.0336 | 0.0456 | 0.0544 | 0 | 0 | 0.0024 |
| SG2 | 0.0744 | 0.0944 | 0.0656 | 0.1136 | 0.1080 | 0.1080 |
| SG3 | 0.0144 | 0.0120 | 0.0120 | 0.1504 | 0.1168 | 0.1392 |
| P1 | 0.0128 | 0.0112 | 0.0152 | 0.1112 | 0.1336 | 0.1304 |
| P2 | 0.0176 | 0.0200 | 0.0248 | 0.0472 | 0.0392 | 0.0504 |
| P3 | 0.0600 | 0.0504 | 0.0408 | 0.0640 | 0.1024 | 0.1472 |

Abbreviations: patient codes in the rows refer to volunteers, whilst columns represent oral rinse treatments, with three independent sampling days 'nested' within each treatment.

Multifactorial Analysis-of-Variance of Difference Spectrophotometric Data Involving the Determination of $ClO_2^-$ Consumption by Salivary Biomolecules Statistical analysis of data acquired regarding the difference spectrophotometric determination of $ClO_2^-$ consumption by salivary biomolecules [i.e., multifactorial analysis-of-variance (ANOVA)] revealed highly significant differences between (1) the $ClO_2^-$ content of each oral rinse investigated ($p<<0.001$), (2) volunteers ($p<0.01$) and (3) 'days nested within volunteers' ($p<0.001$). Indeed, estimates of the overall mean consumption of $ClO_2^-$ determined for a reaction mixture containing a 5:1 (v/v) ratio of oral rinse:human salivary supernatant were $6.334 \times 10^{-2}$ and $1.626 \times 10^{-1}$ μmol. $ClO_2^-$ per ml of salivary supernatant for Oral Rinses I and II respectively. The 'between replicates' mean square value was only $1.266 \times 10^{-4}$, indicating a high level of reproducibility on repeat (triplicate) determinations conducted on each sample tested. The full ANOVA table is shown in Table 2(b).

TABLE 2(b)

Multifactorial analysis-of-variance (ANOVA) table for data acquired from the study involving the difference spectrophotometric determination of $ClO_2^-$ consumption by salivary biomolecules.

| Source of Variation | d.f | SS | MS | F | p | EMS |
|---|---|---|---|---|---|---|
| (1) Between $ClO_2^-$ concentrations (Fixed Effect) | 1 | 1.3839 | 1.3839 | 64.37 | <<0.001 | |
| (2) Between Volunteers (Random Effect) | 19 | 6.5421 | 0.3443 | 2.54 | <0.01 | $\sigma^2 + 6\sigma_o^2 + 18\sigma_v^2$ |
| (3) Between Sampling Days within Volunteers (Random Effect) | 40 | 5.4146 | 0.1354 | 6.30 | <0.001 | $\sigma^2 + 6\sigma_o^2$ |
| (4) Error (Residual) | 295 | 6.3504 | 0.0215 | | | $\sigma^2$ |
| (5) Between Replicates | 4 | $5.065 \times 10^{-4}$ | $1.266 \times 10^{-4}$ | | | |
| Total | 359 | 19.6915 | | | | |

Abbreviations: d.f., degrees-of freedom;
SS, sum of squares values;
MS, mean square values;
F, F variance ratio statistic;
EMS, expected mean square.

Development of a Novel HPLC Method for Monitoring Oral Rinse Chlorite Consumption and its Oxidative Interaction with Salivary Biomolecules In this section, the development of an HPLC method for the determination of $ClO_2^•$ in human saliva specimens (i.e., prior and subsequent to its treatment with the oral rinse formulations) is described.

The chlorite level remaining in each salivary supernatant sample was determined using a high-performance liquid chromatographic (HPLC) technique employing a reversed-phase C18 column with the ion-pair reagent hexadecyl-trimethylammonium bromide (HTB) present in the mobile phase.

Figure 3A:
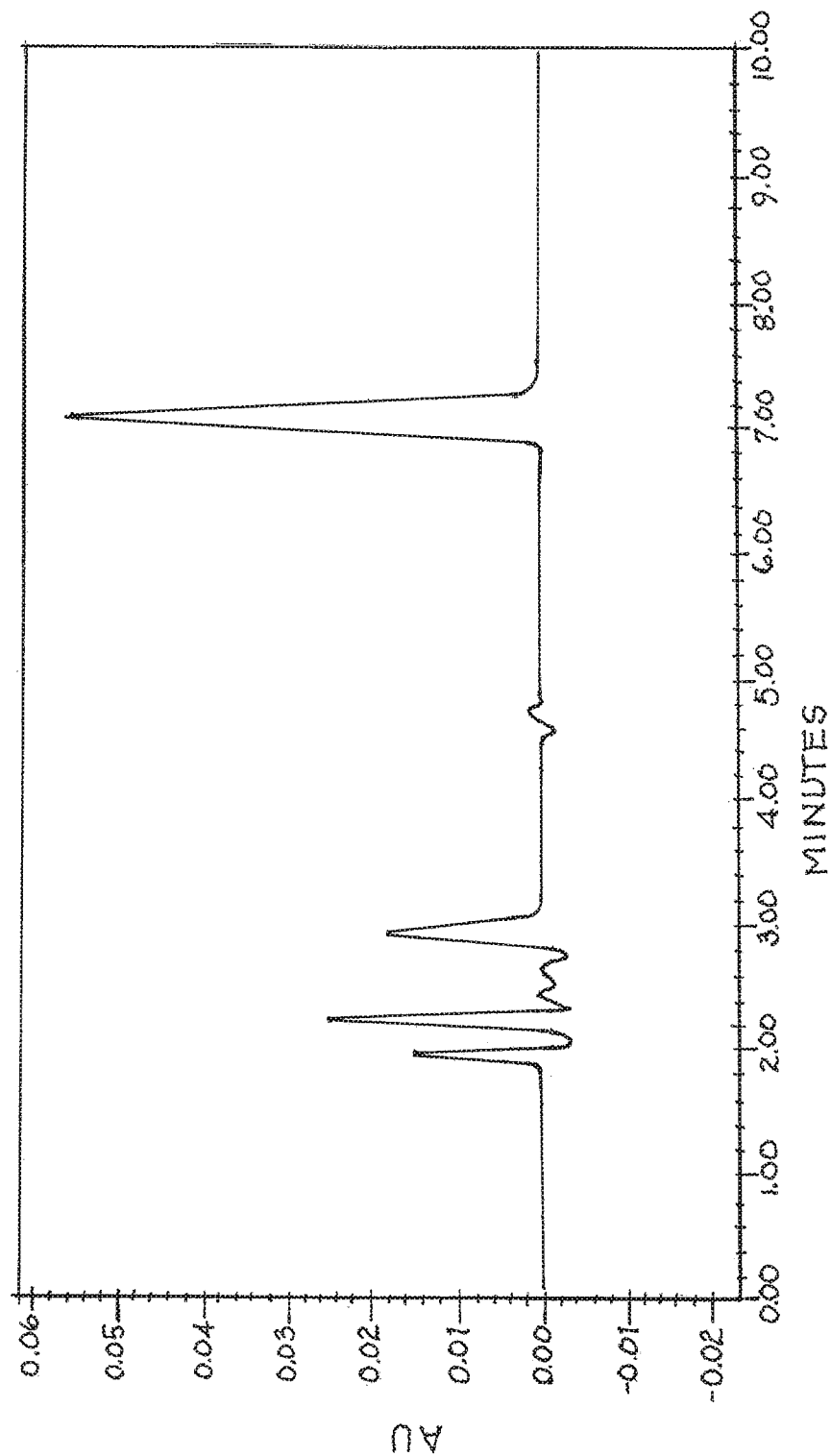
FIG. 3(a) illustrates a reversed-phase (RP) ion-pair (IP) chromatograms of a 1.00 mM chlorite standard solution. The retention time of ClO$_2^-$ was 6.90 min.
Figure 3B:
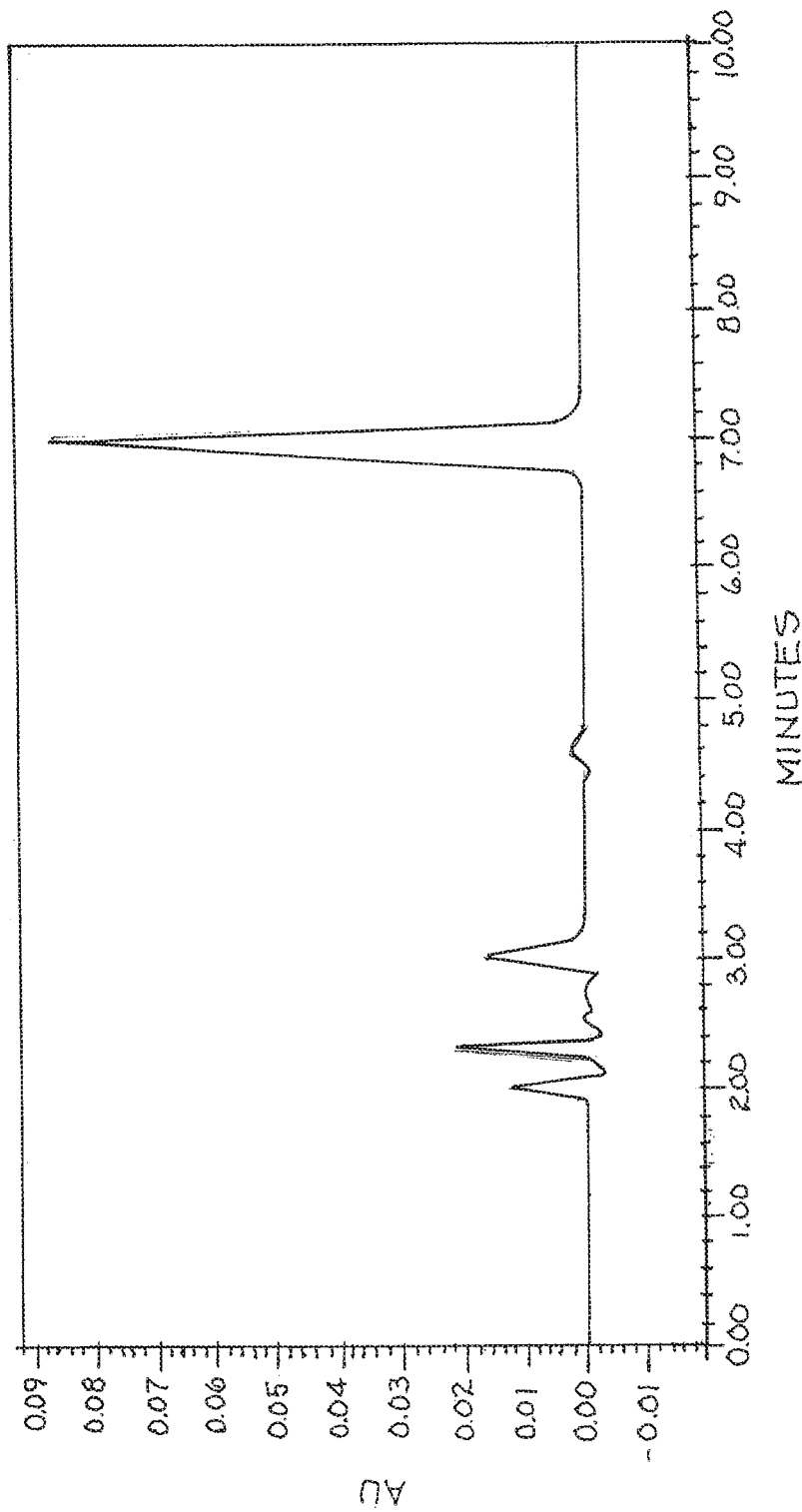
FIG. 3(b) illustrates a reversed-phase (RP) ion-pair (IP) chromatograms of oral rinse I formulation (diluted ¼ with doubly-distilled water prior to analysis). The retention time of ClO$_2^-$ was 6.90 min.
Figure 3C:
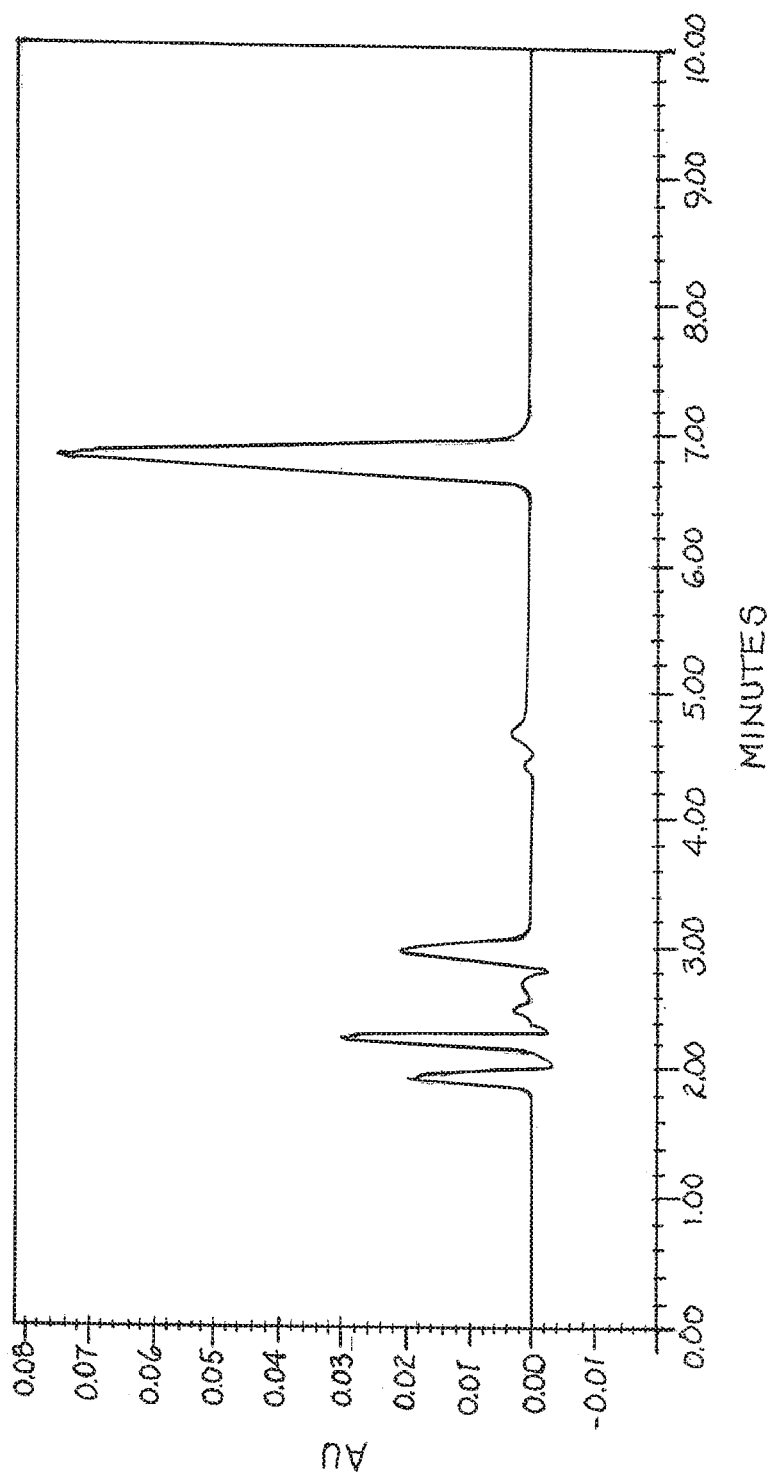
FIG. 3(c) illustrates a reversed-phase (RP) ion-pair (IP) chromatograms of a typical salivary supernatant sample (0.10 ml) pre-treated with 0.50 ml of the above oral rinse I. The retention time of ClO$_2^-$ was 6.90 min.

Experiments involving alteration of the ion pair reagent concentration from 5.00 to 50.00 mM showed that a concentration of 50.00 mM gave rise to a good resolution of $ClO_2^-$ from salivary components in all samples investigated. Identification of the $ClO_2^-$ peak was based on its retention time (6.9 min) and the diode-array spectrum of its HPLC peak ($\lambda_{max}$ 262 nm). Injection of authentic sodium chlorite calibration standards (1.00-10.00 mM) demonstrated a clear linear relationship between peak intensity and concentration. Typical chromatograms of a 1.00 mM chlorite standard solution, the oral rinse I formulation (diluted ¼ with doubly-distilled water prior to analysis) and a typical salivary supernatant sample (0.10 ml) pre-treated with 0.50 ml of the above oral rinse (I) are shown in FIGS. 3(a), (b) and (c) respectively. The retention time of $ClO_2^-$ was 6.90 min.

Figure 4:
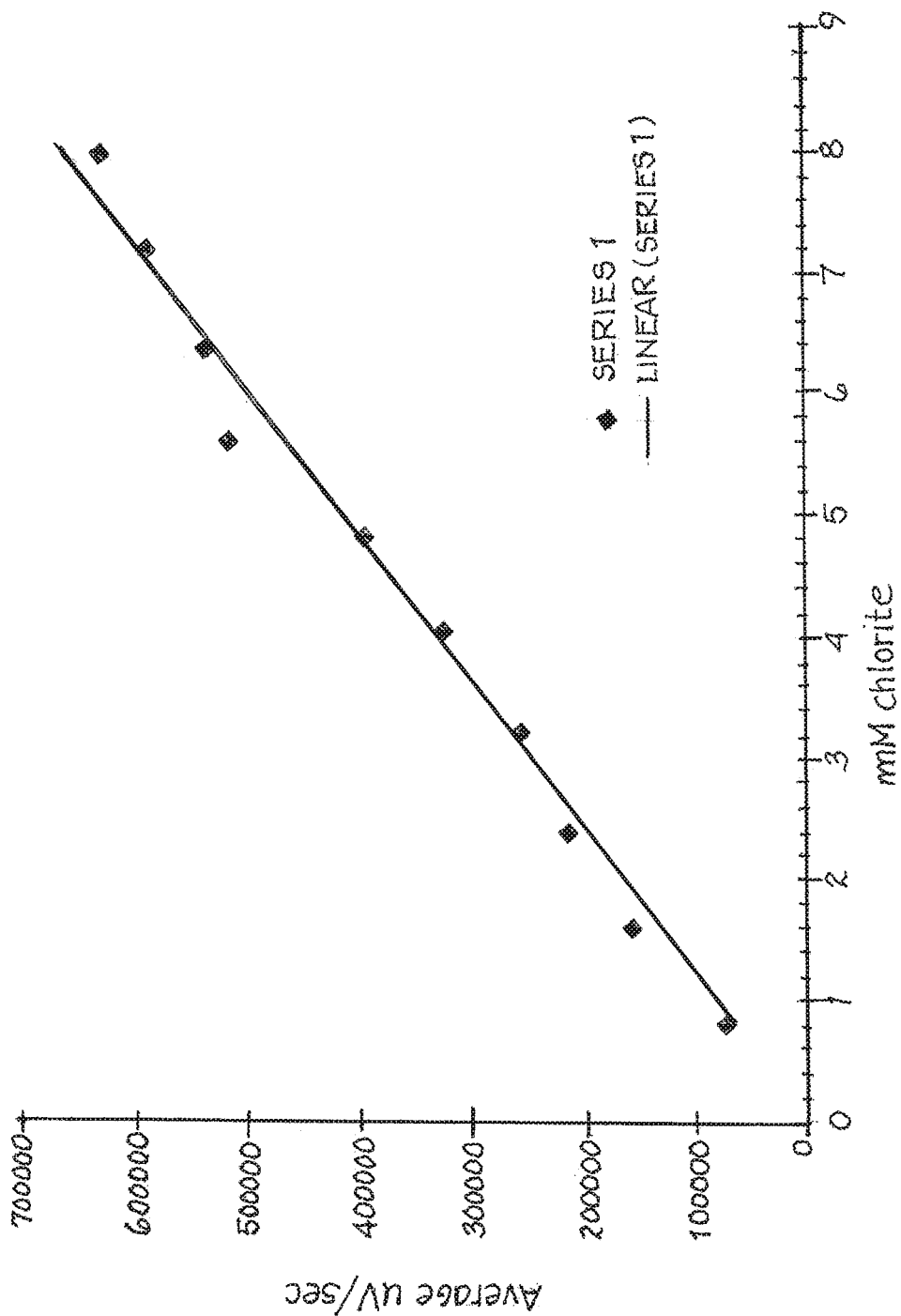
FIG. 4 illustrates a plot of chlorite peak area (μV·s$^{-1}$) obtained from the HPLC analysis versus chlorite concentration for a series of chlorite calibration standards

Plots of chlorite peak area (Table 3) versus its concentration were clearly linear (FIG. 4).

TABLE 3

Area under chlorite peak (µV/sec.) values obtained via HPLC analysis of known chlorite calibration standards

| Concentration (mM) | Mean value | uV/sec | |
|---|---|---|---|
| 0.80 | 70833 | 69102 | 69879 |
| 1.60 | 151673 | 151878 | 153334 |

TABLE 3-continued

Area under chlorite peak (µV/sec.) values obtained via HPLC analysis of known chlorite calibration standards

| Concentration (mM) | Mean value | uV/sec | |
|---|---|---|---|
| 2.40 | 208530 | 209419 | 210975 |
| 3.20 | 259823 | 258413 | 259662 |
| 4.00 | 326322 | 326592 | 326771 |
| 4.80 | 394229 | 394023 | 394386 |
| 5.60 | 514239 | 510086 | 513058 |
| 6.40 | 535511 | 535418 | 530565 |
| 7.20 | 586871 | 592830 | 585209 |
| 8.00 | 628810 | 628254 | 622356 |

CONCLUSIONS

Results acquired on the consumption of (relatively) simple amino acids such as glycine, alanine and taurine by the oral rinse tested here (predominantly containing $ClO_2^-$ as an oxidant) are explicable by previous investigations conducted on the kinetics and mechanisms of the reactions of such biomolecules with oxyhalogen oxidants (including $ClO_2^-$) as outlined below.

Of much relevance to the substantial extent of salivary taurine consumption by the oral rinses investigated in the studies are experiments reported by Chinake and Simoyi (1997) on the oxidation of this β-amino acid by $ClO_2^-$ (at neutral to acidic pH values, i.e., those which are relevant to the oral environment). Indeed, the stoichiometry of this reaction system was found to involve the consumption of 3 molar equivalents of $ClO_2^-$ per mole of taurine to generate 1 of taurine's N-monochloroamine [Cl(H)NCH$_2$CH$_2$SO$_3$H] and 2 of $ClO_2^•$ (the production of N-monochlorotaurine is rapid when expressed relative to that of $ClO_2^•$ accumulation); at the lower pH values investigated, N-monochlorotaurine disassociated to taurine and N-dichlorotaurine. An important characteristic of this reaction system involves a significant induction period in which both HOCl and the reactive intermediate H(OH)NCH$_2$CH$_2$SO$_3$H are produced, a process leading to the formation of N-chlorotaurine and $ClO_2^\bullet$ autocatalytically. As expected for redox reactions involving $ClO_2^-$, this autocatalysis is mediated by a $Cl_2O_2$ intermediate species, and interestingly, taurine's C—S bond is not cleaved, despite the availability of the powerful oxidant HOCl.

Hence, these previously reported studies clearly explain the substantial $^1$H NMR-detectable reductions in salivary taurine observed on treatment of human salivary supernatant specimens with the tested oral rinse $ClO_2^-$. They also indicate that the oral rinse-induced oxidative consumption of a range of α-amino acids present in this biofluid also detected in this investigation, specifically free (non-protein-incorporated) alanine, arginine, aspartate, cysteine, glutamate, glutamine, histidine, hydroxyproline, isoleucine, leucine, lysine, methionine, ornithine, phenylalanine, proline, tyrosine and valine, also proceed via this mechanism.

However, since many $N^\alpha$-monochloroamines generated in this manner are unstable at physiological temperature (37° C.) (Hazen et. al. (1998)), and decompose to corresponding aldehydes (equation 1), and hence further investigations focused on the detection and quantification of such species corresponding to the side-chains of α-amino acids (e.g., formaldehyde from salivary glycine, acetaldehyde from alanine, etc.) are required in order to demonstrate this.

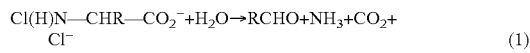

Cl(H)N—CHR—CO$_2^-$+H$_2$O→RCHO+NH$_3$+CO$_2$+Cl$^-$ (1)

Interestingly, it is well known that aldehydes act as potent microbicidal agents, and hence those derived from the above processes may also exert this activity in the oral environment. Indeed, a 2.0% (w/v) solution of this agent is frequently employed as a disinfectant (Follente et. al.).

Similarly, the oxidative consumption of γ-aminobutyrate (GABA) noted here is likely to proceed via a similar mechanism. However, the amino acids cysteine, methionine and tyrosine, each with redox-active side-chains can, of course, also be oxidatively modified by $ClO_2^-$ (and also $ClO_2^\bullet$ and HOCl/OCl$^-$ produced via its reaction with these and/or further α-amino acids, together with GABA and particularly taurine) to cysteine sulphonate (and cysteine), methionine sulphoxide (equation 2) and a tyrosine-derived quinone species respectively.

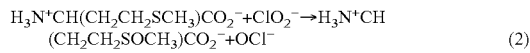

H$_3$N$^+$CH(CH$_2$CH$_2$SCH$_3$)CO$_2^-$+ClO$_2^-$→H$_3$N$^+$CH(CH$_2$CH$_2$SOCH$_3$)CO$_2^-$+OCl$^-$ (2)

With regard to the oxidative consumption of salivary α-keto acid anions, particularly pyruvate and α-ketoglutarte, by $ClO_2^-$ present in the tested oral rinses, which was also observed in our investigations, it has been previously noted that an intense green Cl$_2$/OCl$^-$ colouration is generated on reaction of $ClO_2^-$ with pyruvate (equation 3) [Lynch et. al. 1997]. Hence, such reaction systems clearly generate HOCl/OCl$^-$ which can, of course, subsequently produce N-monochloro- and -dichloroamines from free or, in selected cases, protein-incorporated amino acids, the former decomposing to corresponding aldehydes under physiological conditions.

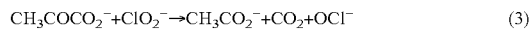

CH$_3$COCO$_2^-$+ClO$_2^-$→CH$_3$CO$_2^-$+CO$_2$+OCl$^-$ (3)

Therefore, it should be noted that the production of reactive HOCl/OCl$^-$ during an induction period observed during the reaction of $ClO_2^-$ with the β-amino acid taurine (Chinake and Simoyi (1997)) (and also presumably the salivary α-amino acids and γ-aminobutyrate consumed on reaction with tested oral rinse $ClO_2^-$) will also serve to further reduce the amino acid concentrations of human saliva. Indeed, even if this mechanistic process only proceeds in the reactions of selected free amino acids with $ClO_2^-$ (or those located at the N-termini of salivary proteins), the HOCl/OCl$^-$ generated will, of course, be available to react with a much wider range of such HOCl/OCl$^-$ 'scavenger' species in a (relatively) unselective manner to form $N^\alpha$-monochloro- and dichloroamines, together with $N^\epsilon$-monochloro- and -dichloroamines in lysine residues (either free or protein-incorporated). As noted above, specific aldehydes arising from the decomposition of their parent amino acid $N^\alpha$-monochloroamine precursors will serve as valuable indicators of the activity of HOCl/OCl$^-$ arising from these reaction systems (RCHO, where R represents an amino acid side-chain moiety).

Aldehydes produced from the interaction of HOCl/OCl$^-$ with salivary α-amino acids and the decomposition of the primary $N^\alpha$-monochloroamine products can also react with $ClO_2^-$, and the oxidation of formaldehyde (HCHO) by this oxyhalogen oxidant was critically examined by Chinake et. al. (1998) in both mildly acidic and alkaline media. This reaction gave rise to CO$_2$ and $ClO_2^\bullet$ as products, the latter in virtually quantitative yield, and was autocatalytic with respect to hypochlorous acid/hypochlorite (HOCl/OCl$^-$). Indeed, the primary phase of the process generated HOCl which facilitated (catalysed) the production of $ClO_2^\bullet$ and the additional oxidation of formic acid/formate (HCO$_2$H/HCO$_2^-$); $ClO_2^\bullet$ rapidly accumulated in view of its (relative) lack of reactivity towards both HCHO and HCO$_2$H/HCO$_2^-$. Although with excess HCHO the stoichiometry of this process was determined to be $3ClO_2^-$+HCHO→HCO$_2$H+$2ClO_{2\,(aq.)}^\bullet$+Cl$^-$+2H$_2$O, when large excesses of $ClO_2^-$ were present [as, of course, expected in the case of 5:1 (v/v) mixtures of tested oral rinses:human salivary supernatant], the stoichiometric profile involved in the consumption of 6 molar equivalents of $ClO_2^-$ per mole of HCHO to generate 4 of $ClO_2^\bullet$, 2 of Cl$^-$ and 1 of CO$_2$.

With regard to the oral rinse-mediated decrease in the intensities of salivary cysteine resonances observed here (and also in previously-conducted chemical model studies (Lynch et. al., 1997), Darkwa et. al. (2003) investigated the oxidative consumption of N-acetylcysteine by $ClO_2^-$, and found that the final product generated from this reaction system was N-acetylsulphonate and that the process had a stoichiometry of $3ClO_2^-$+2RSH→3Cl$^-$+2RSO$_3$H; as expected, there was no evidence for the production of N-chloroamine derivatives. This oxidation proceeds via a mechanism involving a stepwise S-oxygenation process involving the consecutive generation of sulphenic and sulphonic acid adducts. Intriguingly, a notable characteristic of the reaction is the rapid, immediate formation of chlorine dioxide ($ClO_2^\bullet$) without a monitorable induction period since oxidation of the thiol by this oxyhalogen free radical species is sufficiently slow for it to accumulate without such a time lag which, in general, represents a characteristic of the oxidation of organosulphur compounds by $ClO_2^-$. A full description of the 'global' dynamics of this system involves 8 reactions in a truncated mechanism.

In conclusion, evidence provided in our investigations clearly demonstrate that the generation of $ClO_2^\bullet$ from $ClO_2^-$ in the oral environment is not entirely dependent on entry of the latter into acidotic environments therein (equations 4 and 5, the pK$_a$ value of the $ClO_2^-$/HClO$_2$ system being 2.31 (Lynch et al. 1997)). Although the mean pH value of this biofluid is ca. 7 when unchallenged with oral stimuli (i.e., 'resting'), the consumption of relatively large volumes of beverages of lower pH value (ca. pH 4) can clearly exert a significant influence on this parameter. However, it should also be noted that the pH value of primary root caries lesions can approach a limit of 4.5, and therefore this represents an environment in which there are expected to be marked elevations in the level of $HClO_2$ generated (i.e., from 0.0020% at pH 7.00 to 0.64% of total available oxyhalogen oxidant at pH 4.50), although it should be noted that, in view of the $pK_a$ value of the $ClO_2^-/HClO_2$ couple, this value still remains very low when expressed relative the total amount of oxyhalogen oxidant available (the remainder being $ClO_2^-$ in the absence of alternative means of producing $ClO_2^{\bullet}$, or $HOCl/OCl^-$, from the interaction of $ClO_2^-$ with α-, β- and γ-amino acids available). Of course, from the stoichiometry of equation 5, 2 molar equivalents of $ClO_2^{\bullet}$ are generated per 4 of $HClO_2$, and hence the above figures for $HClO_2$ generation represent double that of the total $ClO_2^{\bullet}$ producible (i.e., maximum percentages of 0.0010 and 0.32% of total oxyhalogen oxidant at pH values of 7.00 and 4.50 respectively). Clearly, the rate of $ClO_2^{\bullet}$ generation from $HClO_2$ should also be considered in view of the short oral rinse-salivary supernatant equilibration time involved in our studies.

$ClO_2^- + H^+ \rightarrow HClO_2 (pK_a=2.31)$ (4)

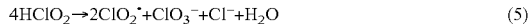

$4HClO_2 \rightarrow 2ClO_2^{\bullet} + ClO_3^- + Cl^- + H_2O$ (5)

We claim:

1. A method for treatment of the oral cavity, the method comprising the steps of:
    (a) applying to the oral cavity an aqueous buffered oral care composition comprising (i) aqueous sodium chlorite in a concentration of about 0.05% (w/v) to about 0.2% (w/v), and (ii) an aqueous buffer comprising a citrate and a base comprising at least one of acetate and formate, wherein the buffer is present in the composition in a quantity sufficient to maintain the stability of the sodium chlorite in the composition until the composition is acidified in the oral cavity, wherein the aqueous buffered oral care composition contains no more than trace amounts of hypochlorite; and
    (b) mixing the buffered oral care composition from step (a) with salivary biomolecules present in the oral cavity to activate and release chlorine dioxide gas from the composition rapidly and without a period of induction, for reducing growth and development of oral bacteria and microorganisms resident in the oral cavity.

2. The method of claim 1, wherein the buffer further comprises a peroxy compound.

3. The method of claim 1, wherein the composition has a 1% or less change in the amount of UV/visible absorbance spectra at $\lambda_{max}=262$ nm at 72 hours after formulation as compared to the amount of UV/visible absorbance spectra at 0 hours after formulation.

4. A buffered oral care composition comprising (a) sodium chlorite in a concentration of about 0.05% (w/v) to about 0.2% (w/v), and (b) a buffer comprising a citrate and a base comprising at least one of acetate and formate, wherein the buffer is present in the composition in a quantity sufficient to maintain the stability of the sodium chlorite in the composition until the composition is acidified in the oral cavity, and wherein activation and release of chlorine dioxide gas from the composition occurs rapidly and without a period of induction, wherein the buffered oral care composition contains no more than trace amounts of hypochlorite.

5. The oral care composition of claim 4, further comprising a peroxy compound.

6. The composition as set forth in claim 4, wherein the composition has a 1% or less change in the amount of UV/visible absorbance spectra at $\lambda_{max}=262$ nm at 72 hours after formulation as compared to the amount of UV/visible absorbance spectra at 0 hours after formulation.

7. The method of claim 1, wherein the chlorine dioxide gas is immediately released upon contact with the oral cavity.

8. The buffered oral care composition of claim 4, wherein the chlorine dioxide gas is immediately released upon contact with the oral cavity.

9. The method of claim 1, wherein the buffered oral care composition is one of the group consisting of a wash, a rinse, a soak, a paste, a gel, and an aerosol spray.

10. The buffered oral care composition of claim 4, wherein the composition is one of the group consisting of a wash, a rinse, a soak, a paste, a gel, and an aerosol spray.

* * * * *